(12) United States Patent
Deaton et al.

(10) Patent No.: US 11,065,006 B2
(45) Date of Patent: Jul. 20, 2021

(54) DUAL INFLATABLE ARTERIAL PROSTHESIS

(71) Applicant: Endologix LLC, Irvine, CA (US)

(72) Inventors: David Deaton, Crownsville, MD (US); Eric Noda, Rancho Santa Margarita, CA (US); Carlos Ortega, Irvine, CA (US); Girma Kebede, Irvine, CA (US); Kaushik Patel, Poway, CA (US); Swanand Sardesai, Anaheim Hills, CA (US)

(73) Assignee: Endologix LLC, Irvine, CA (US)

( * ) Notice: Subject to any disclaimer, the term of this patent is extended or adjusted under 35 U.S.C. 154(b) by 239 days.

(21) Appl. No.: 15/540,246

(22) PCT Filed: Dec. 30, 2015

(86) PCT No.: PCT/US2015/068204
§ 371 (c)(1),
(2) Date: Jun. 27, 2017

(87) PCT Pub. No.: WO2016/109757
PCT Pub. Date: Jul. 7, 2016

(65) Prior Publication Data
US 2018/0021045 A1     Jan. 25, 2018

Related U.S. Application Data

(60) Provisional application No. 62/099,072, filed on Dec. 31, 2014.

(51) Int. Cl.
*A61F 2/07* (2013.01)
*A61B 17/12* (2006.01)

(52) U.S. Cl.
CPC .. *A61B 17/12113* (2013.01); *A61B 17/12118* (2013.01); *A61B 17/12136* (2013.01);
(Continued)

(58) Field of Classification Search
CPC ................................. A61F 2/07; A61F 2/0004
(Continued)

(56) References Cited

U.S. PATENT DOCUMENTS 6,827,735 B2 * 12/2004 Greenberg ....... A61B 17/12109
623/1.25
8,216,297 B2 * 7/2012 Kari .......................... A61F 2/07
623/1.25
(Continued)

FOREIGN PATENT DOCUMENTS

CN      102946825 A      2/2013
CN      103648437 A      3/2014
(Continued)

OTHER PUBLICATIONS

International Preliminary Report on Patentability dated Jul. 13, 2017, from application No. PCT/US2015/068204.
(Continued)

*Primary Examiner* — Suzette J Gherbi
(74) *Attorney, Agent, or Firm* — Foley & Lardner LLP

(57) ABSTRACT

A system includes an inner filling structure around a stent-structure and an outer filling structure around the inner filling structure. The inner filling structure can be configured to produce a proximal seal with a first portion of an artery at a proximal end and a distal seal with a second portion of an artery at a distal end when the inner filling structure is in an inflated state. The outer filling structure can have an inner surface surrounding at least a portion of the inner filling structure. The outer filling structure can be configured to be inflatable to occupy a space within an aneurysm at a lower pressure than a pressure in the inner filling structure.

13 Claims, 19 Drawing Sheets

(52) U.S. Cl.
CPC ........ *A61F 2/07* (2013.01); *A61B 2017/1205* (2013.01); *A61F 2002/077* (2013.01); *A61F 2210/0076* (2013.01); *A61F 2220/0075* (2013.01); *A61F 2230/0067* (2013.01); *A61F 2230/0095* (2013.01); *A61F 2250/0003* (2013.01); *A61F 2250/0018* (2013.01); *A61F 2250/0019* (2013.01); *A61F 2250/0039* (2013.01); *A61F 2250/0048* (2013.01)

(58) Field of Classification Search
USPC .............................................. 623/1.15–1.35
See application file for complete search history.

(56) References Cited

U.S. PATENT DOCUMENTS

| | | | |
|---|---|---|---|
| 9,415,195 B2* | 8/2016 | Schreck | A61M 25/104 |
| 2002/0168331 A1 | 11/2002 | Whalen et al. | |
| 2005/0171597 A1 | 8/2005 | Boatman et al. | |
| 2009/0287145 A1 | 11/2009 | Cragg et al. | |
| 2011/0276078 A1* | 11/2011 | Rao | A61F 2/07 |
| | | | 606/194 |
| 2012/0016456 A1 | 1/2012 | Herbowy et al. | |
| 2012/0259406 A1* | 10/2012 | Schreck | A61M 25/09 |
| | | | 623/1.27 |
| 2013/0071550 A1* | 3/2013 | Edwin | A61L 27/16 |
| | | | 427/2.25 |
| 2016/0158040 A1* | 6/2016 | Zupkofska | A61F 2/82 |
| | | | 623/23.7 |
| 2017/0007263 A1* | 1/2017 | Schreck | A61B 17/12036 |
| 2017/0112611 A1* | 4/2017 | Edwin | A61F 2/94 |
| 2018/0021045 A1* | 1/2018 | Deaton | A61B 17/12113 |
| | | | 623/1.15 |
| 2018/0125644 A1* | 5/2018 | Conklin | A61F 2/243 |
| 2018/0311057 A1* | 11/2018 | Tyagi | A61F 2/91 |

FOREIGN PATENT DOCUMENTS

| | | | |
|---|---|---|---|
| JP | 2013-516232 A | 5/2013 | |
| JP | 2014-517730 A | 7/2014 | |

OTHER PUBLICATIONS

Chinese Office Action dated Jul. 3, 2018, from application No. 201580076390.3.
Extended European Search Report dated Oct. 12, 2018, from application No. 15876323.5.
International Search Report and Written Opinion dated Feb. 25, 2016, from application No. PCT/US2015/068204.
Chinese Office Action dated Mar. 15, 2019, from application No. 201580076390.3.
Chinese Office Action dated Oct. 18, 2019, from application No. 201580076390.3.
Japanese Office Action dated Oct. 29, 2019, from application No. 2017-534803.
Japanese Office Action dated Jun. 30, 2020, from application No. 2017-534803.
Extended European Search Report dated Sep. 9, 2020, from application No. 20181569.3.
Chinese Office Action dated May 7, 2020, from application No. 201580076390.3.

\* cited by examiner

DUAL INFLATABLE ARTERIAL PROSTHESIS

CROSS-REFERENCE TO RELATED PATENT APPLICATION

This application claims priority from U.S. Provisional Patent Application No. 62/099,072, filed Dec. 31, 2014, the entire contents of which are incorporated by reference herein.

FIELD

Various embodiments disclosed herein relate generally to medical apparatuses and methods for treatment of arterial disease. More particularly, various embodiments relate to expandable prostheses and methods for treating abdominal and other aneurysms. Various embodiments relate to devices and methods of treating an abdominal, paravisceral, or thoracic aneurysm.

BACKGROUND

Aneurysms are enlargements or "bulges" in blood vessels which are often prone to rupture and which therefore present a serious risk to the patient. Aneurysms may occur in any blood vessel but are of particular concern when they occur in the cerebral vasculature or the patient's aorta.

Some embodiments of the present disclosure are concerned with aneurysms occurring in the aorta, particularly those referred to as aortic aneurysms. Abdominal aortic aneurysms (AAA's) are classified based on their location within the aorta as well as their shape and complexity. Aneurysms which are found below the renal arteries are referred to as infrarenal abdominal aortic aneurysms. Suprarenal abdominal aortic aneurysms occur above the renal arteries, while thoracic aortic aneurysms (TAA's) occur in the ascending, transverse, or descending part of the upper aorta.

Infrarenal aneurysms are the most common, representing about seventy percent (70%) of all aortic aneurysms. Suprarenal aneurysms are less common, representing about twenty percent (20%) of the aortic aneurysms. Thoracic aortic aneurysms are the least common and often the most difficult to treat. Most endovascular systems are also too large (above 12 French) for percutaneous introduction.

The most common form of aneurysm is "fusiform," wherein the enlargement extends about the entire aortic circumference. Less commonly, the aneurysms may be characterized by a bulge on one side of the blood vessel attached at a narrow neck. Thoracic aortic aneurysms are often dissecting aneurysms caused by hemorrhagic separation in the aortic wall, usually within the medial layer. The most common treatment for each of these types and forms of aneurysm is open surgical repair. Open surgical repair is quite successful in patients who are otherwise reasonably healthy and free from significant co-morbidities. Such open surgical procedures are problematic, however, since access to the abdominal and thoracic aortas is difficult to obtain and because the aorta must be clamped off, placing significant strain on the patient's heart.

Endoluminal grafts can be used for the treatment of aortic aneurysms in patients who cannot undergo open surgical procedures. In general, endoluminal repairs access the aneurysm "endoluminally" through either or both iliac arteries in the groin. The grafts, which can have fabric or membrane tubes supported and attached by various stent structures, are then implanted, and can require several pieces or modules to be assembled in situ. Successful endoluminal procedures can have a much shorter recovery period than open surgical procedures.

SUMMARY

The following summary is illustrative only and is not intended to be in any way limiting. In addition to the illustrative aspects, embodiments, and features described below, further aspects, embodiments, and features will become apparent by reference to the following drawings and the detailed description.

An exemplary device includes an inner filling structure around a stent and an outer filling structure around the inner filling structure. The inner filling structure can be configured to produce a proximal seal with a first portion of an artery at a proximal end and a distal seal with a second portion of an artery at a distal end. In various embodiments, the inner filling structure is inflatable to produce the proximal seal and the distal seal at high pressures such as 300 to 600 mm Hg. The outer filling structure can have an inner surface surrounding a portion of the inner filling structure. In some embodiments, the outer filling structure is configured to occupy a space within an aneurysm at lower pressures such as 50 to 120 mm Hg. In various embodiments, the outer filling structure is inflatable to occupy the space within the aneurysm. The inner filling structure and the outer filling structure may have differential pressure. In some embodiments, the inner filling structure has a higher pressure than the outer filling structure.

A system in accordance with an embodiment includes an inner filling structure and an outer filling structure. In various embodiments, the inner filling structure is inflatable to produce a first seal with a first portion of an artery at a first end of the inner filling structure. In various embodiments, the outer filling structure has an inner surface that surrounds at least a portion of the inner filling structure, and the outer filling structure is inflatable to occupy a space within an aneurysm. In some embodiments, the inner filling structure is inflatable to produce a second seal with a second portion of the artery at a second end of the inner filling structure.

In various embodiments, a pressure within the inner filling structure when the inner filling structure is in an inflated state is higher than a pressure within the outer filling structure when the outer filling structure is in an inflated state. In some embodiments, the inner filling structure comprises a semi-compliant material that is less compliant than a material of the outer filling structure. In various embodiments, the inner filling structure is configured to be inflatable to a pressure in a range of 300 to 600 mm Hg, and the outer filling structure is configured to be inflatable to a pressure in a range of 50 to 120 mm Hg. In some embodiments, the inner filling structure is fillable with a hardenable material to a pressure that is higher than a pressure in the outer filling structure.

In various embodiments, the inner filling structure is configured to overlap a healthy region of the artery that is proximal the aneurysm. In some embodiments, the outer filling structure is configured to contact a wall of the aneurysm after being filled to a pressure that is lower than a pressure in the inner filling structure. In some embodiments, the first end of the inner filling structure extends beyond an end of the outer filling structure. In various embodiments, the inner filling structure and the outer filling structure are attached to a stent. In some embodiments, the inner filling structure has a hardness of at least about 55D shore-A. In some embodiments, the outer filling structure has a hardness of at least about 70 shore-A or 77 shore-A.

A system in accordance with an embodiment includes a stent, an inner filling structure, and an outer filling structure. In various embodiments, the inner filling structure is attached to the stent, and the inner filling structure inflatable with a filling medium. In various embodiments, the outer filling structure has an inner surface that surrounds at least a portion of the inner filling structure, and the outer filling structure is inflatable to occupy a space within an aneurysm. In some embodiments, the system further includes a first fill line connected to the inner filling structure and a second fill line connected to the outer filling structure.

In various embodiments, the inner filling structure is attached to the stent by sutures. In some embodiments, the outer filling structure is directly attached to the stent. In some embodiments, the outer filling structure is directly attached to an outer surface of the inner filling structure. In various embodiments, a portion of the stent extends beyond an end of the inner filling structure and an end of the outer filling structure. In some embodiments, the inner filling structure is configured such that a diameter of the inner filling structure varies along a length of the inner filling structure when the inner filling structure is in an inflated state. In various embodiments, the inner filling structure is configured such that a diameter of a proximal end of the inner filling structure is greater than a diameter of a distal end of the inner filling structure when the inner filling structure is in an inflated state.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Figure 1A:
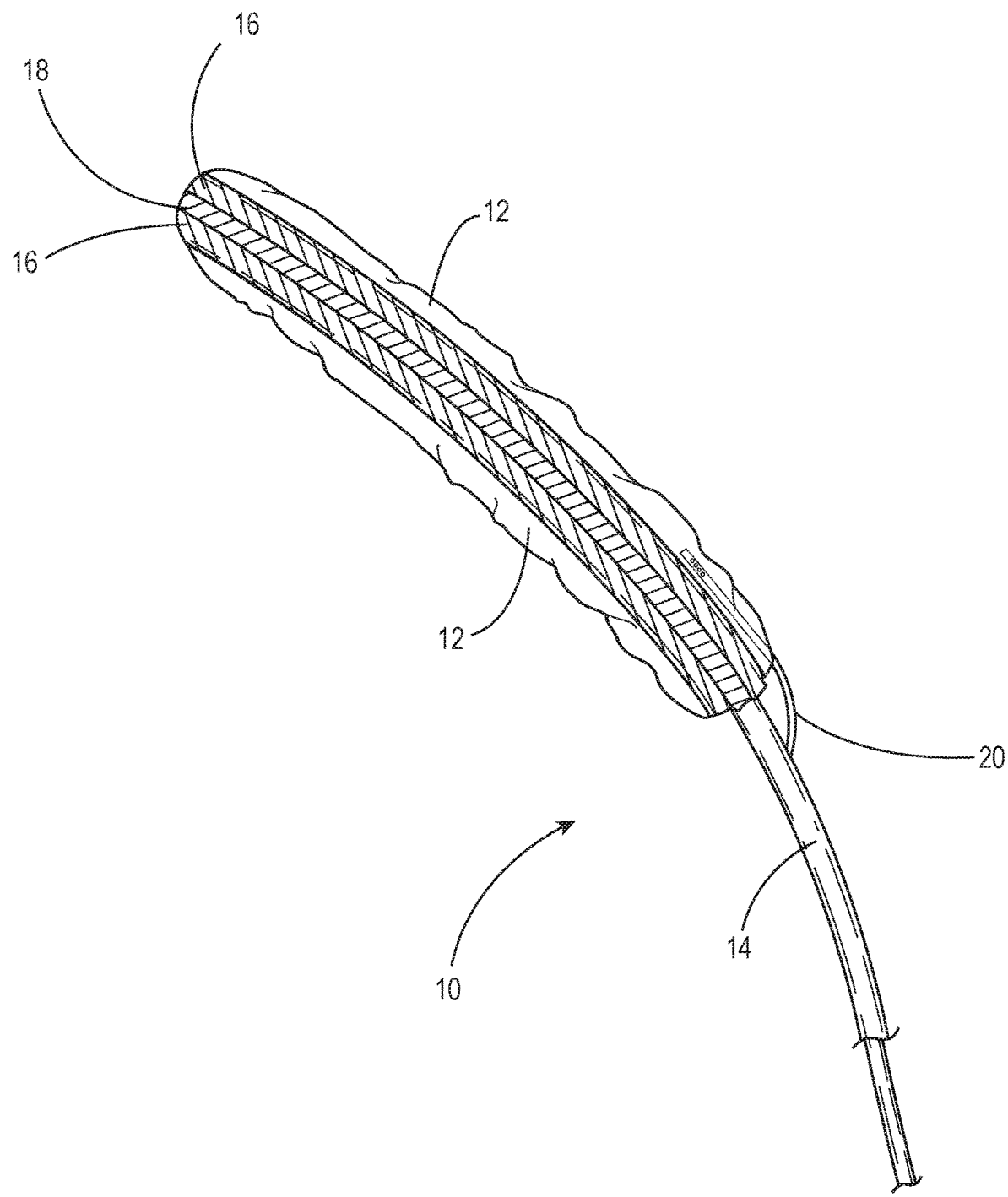
FIGS. 1A and 1B are an illustration of a dual inflatable single prosthesis in accordance with an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Figure 1B:
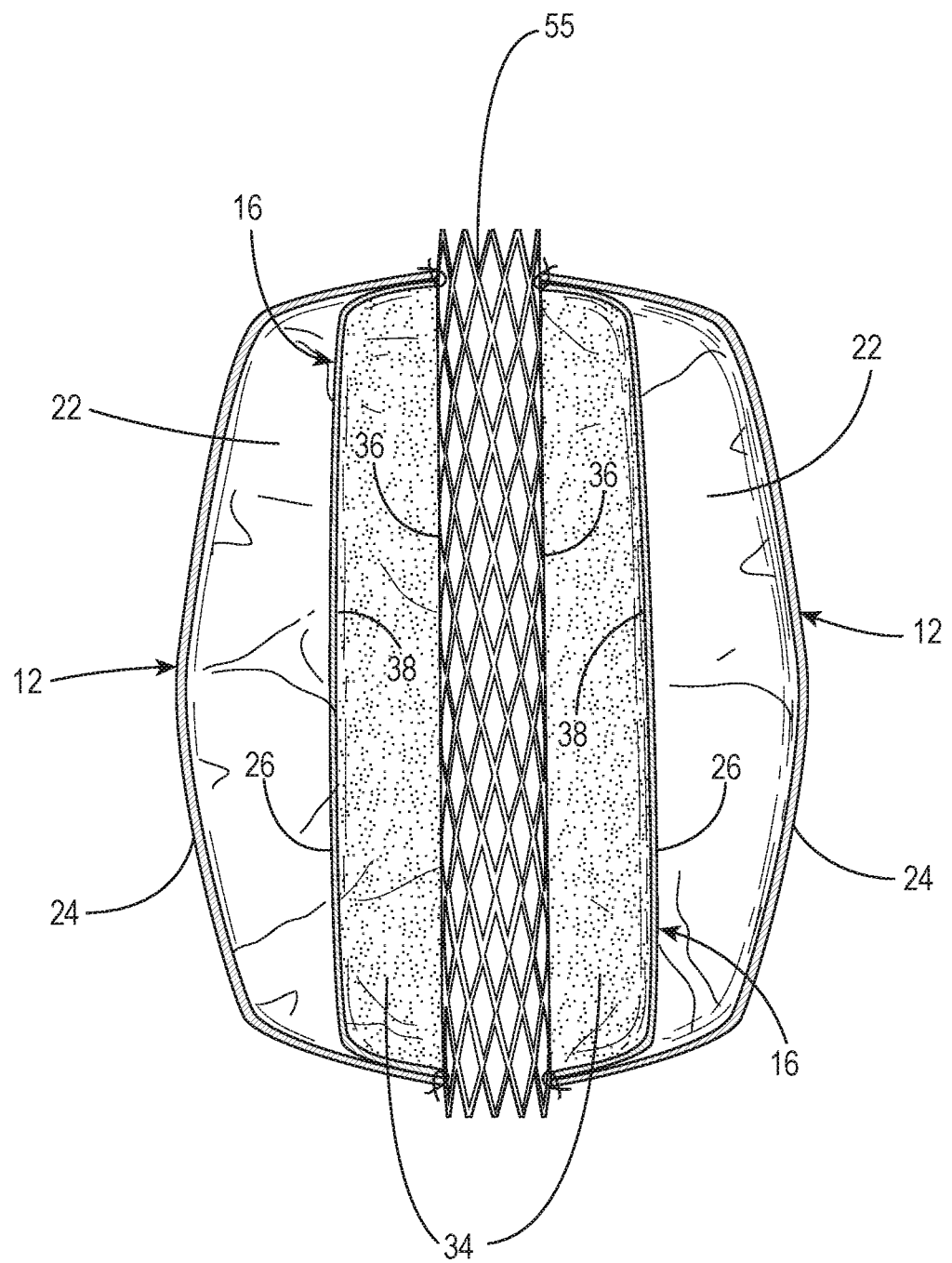

FIG. 1A is an illustration of a dual inflatable single prosthesis in an uninflated state in accordance with an illustrative embodiment. FIG. 1B is an illustration of the dual inflatable single prosthesis of FIG. 1A in an inflated state in accordance with an illustrative embodiment. With reference to FIGS. 1A and 1B, a system 10, in accordance with the principles of the present disclosure, can deliver a double-walled filling structure to an aneurysm and can include a delivery catheter 14. The delivery catheter 14 can comprise a stent 18, a balloon inflation lumen (not illustrated) or other structure for expanding expandable components, and a filling tube 20 for delivering a filling medium (e.g. polymer or hydrogel) or material to an internal space 22 of an outer filling structure 12. The internal space 22 of the outer filling structure 12 can be defined between an outer wall 24 of the outer filling structure 12 and an inner wall 26 of the outer filling structure 12. Upon inflation with the filling material or medium, the outer wall 24 of the outer filling structure 12 may expand radially, as can the inner wall 26 of the outer filling structure 12.

An inner filling structure 16 can comprise an internal space or volume 34 defined by an inner wall 36 of the inner filling structure 16 and an outer wall 38 of the inner filling structure 16. Upon inflation with the filling material or medium, the outer wall 38 of the inner filling structure 16 can expand radially, as can the inner wall 36 of the inner filling structure 16. Upon inflation, the inner wall 36 of the inner filling structure 16 can form a lumen 55.

The inner filling structure 16 and the outer filling structure 12 can be disposed on a proximal end of the system 10. In an illustrative embodiment, the inner filling structure 16 can extend beyond the outer filling structure 12 at both a proximal end of the inner filling structure 16 and a distal end of the inner filling structure 16. In other embodiments, the inner filling structure 16 can have a same length as the outer filling structure 12. In other embodiments, the inner filling structure 16 can extend beyond the outer filling structure 12 at either the proximal end of the inner filling structure 16 or the distal end of the inner filling structure 16.

The inner filling structure 16 can be an expandable balloon or other structure. The outer filling structure 12 can also be an expandable balloon or other structure. In an illustrative embodiment, the inner filling structure 16 can be independently inflated using a fill tube (or concentric filling tube) from the outer filling structure 12. In other embodiments, the inner filling structure 16 can be inflated simultaneously with the outer filling structure 12. Regardless of whether the inner filling structure 16 and the outer filling structure 12 are inflated independently or simultaneously, the inner filling structure 16 and the outer filling structure 12 can be filled to have either an equal or approximately equal pressure or different pressures. In an illustrative embodiment, the inner filling structure 16 can be independently inflated to have a first filling pressure, and the outer filling structure 12 can be independently inflated to have a second filling pressure. In some embodiments, the first filling pressure can be greater than the second filling pressure. In some embodiments, the second filling pressure may be 1 atmosphere, while the first filling pressure may be greater than 1 atmosphere. In other embodiments, the first filling pressure can be less than the second filling pressure. In some embodiments, the second filling pressure may be in a range of 50 to 120 mm Hg, while the first filling pressure may be greater than that pressure such as in a range of 300 to 600 mm Hg.

In an illustrative embodiment, the outer filling structure 12 can have a first filling lumen that can extend from the delivery catheter 14 into the outer filling structure 12. The first filling lumen can be configured to introduce a filling material, such as a polymer or hydrogel, into the internal space 22 of the outer filling structure 12. The first filling lumen can also be configured to be removed from the outer filling structure 12 while maintaining the filling material inside of the outer filling structure 12 after the first filling lumen is removed. The first filling lumen can be configured to expand the outer filling structure 12 by introducing the filling material.

In an illustrative embodiment, the inner filling structure 16 can have a second filling lumen that can extend from the delivery catheter 14 into the inner filling structure 16. The second filling lumen can be configured to introduce a filling material into the internal space 34 of the inner filling structure 16. The second filling lumen can also be configured to be removed from the inner filling structure 16 while maintaining the filling material inside of the inner filling structure 16 after the second filling lumen is removed. The second filling lumen can be configured to expand the inner filling structure 16 by introducing the filling material. In some embodiments, the inner filling structure 16 can be filled with a different filling material than the outer filling structure 12. In other embodiments, the inner filling structure 16 can be filled with the same filling material as the outer filling structure 12.

In some embodiments, the outer filling structure 12 can have a first filling lumen and the inner filling structure 16 can have a second filling lumen. The first filling lumen can extend from the delivery catheter 14 directly to the outer filling structure 12. The second filling lumen can extend from the delivery catheter 14 directly to the inner filling structure 16. In other embodiments, the second filling lumen can extend from the delivery catheter 14 to the outer filling structure 12 through the inner filling structure 16. In some embodiments, the first filling lumen can be a parallel lumen to the second filling lumen. In other embodiments, the first filling lumen and the second filling lumen can be coaxial. For example, the second filling lumen can extend from the delivery catheter 14 directly to the inner filling structure 16. Within the second filling lumen can be the first filling lumen, extending from the delivery catheter 14, through the inner filling structure 16, to the outer filling structure 12.

In an illustrative embodiment, a filling lumen can be configured to introduce a filling material into both the inner filling structure 16 and the outer filling structure 12. In one embodiment, the filling lumen can be configured to inflate the inner filling structure 16 by introducing the filling material, and be configured to be removed from the inner filling structure 16 while maintaining the filling material within the inner filling structure 16. The filling lumen can also be configured to inflate the outer filling structure 12 by introducing the filling material, and be configured to be removed from the outer filling structure 12 while maintaining the filling material within the outer filling structure 12. In an embodiment, the filling lumen can be configured to inflate the inner filling structure 16 before inflating the outer filling structure 12. In other embodiments, the filling lumen can be configured to inflate the inner filling structure 16 after inflating the outer filling structure 12. In yet another embodiment, the filling lumen can be configured to inflate the inner filling structure 16 at the same time as the outer filling structure 12. In an illustrative embodiment, the filling lumen can be configured to fill the inner filling structure 16 to a first filling pressure, and fill the outer filling structure 12 to a second filling pressure. In various embodiments, the first filling pressure is different from the second filling pressure. The filling lumen can be configured to be removed from the inner filling structure 16 and the outer filling structure 12 while maintaining the first filling pressure and the second filling pressure.

Figure 2:
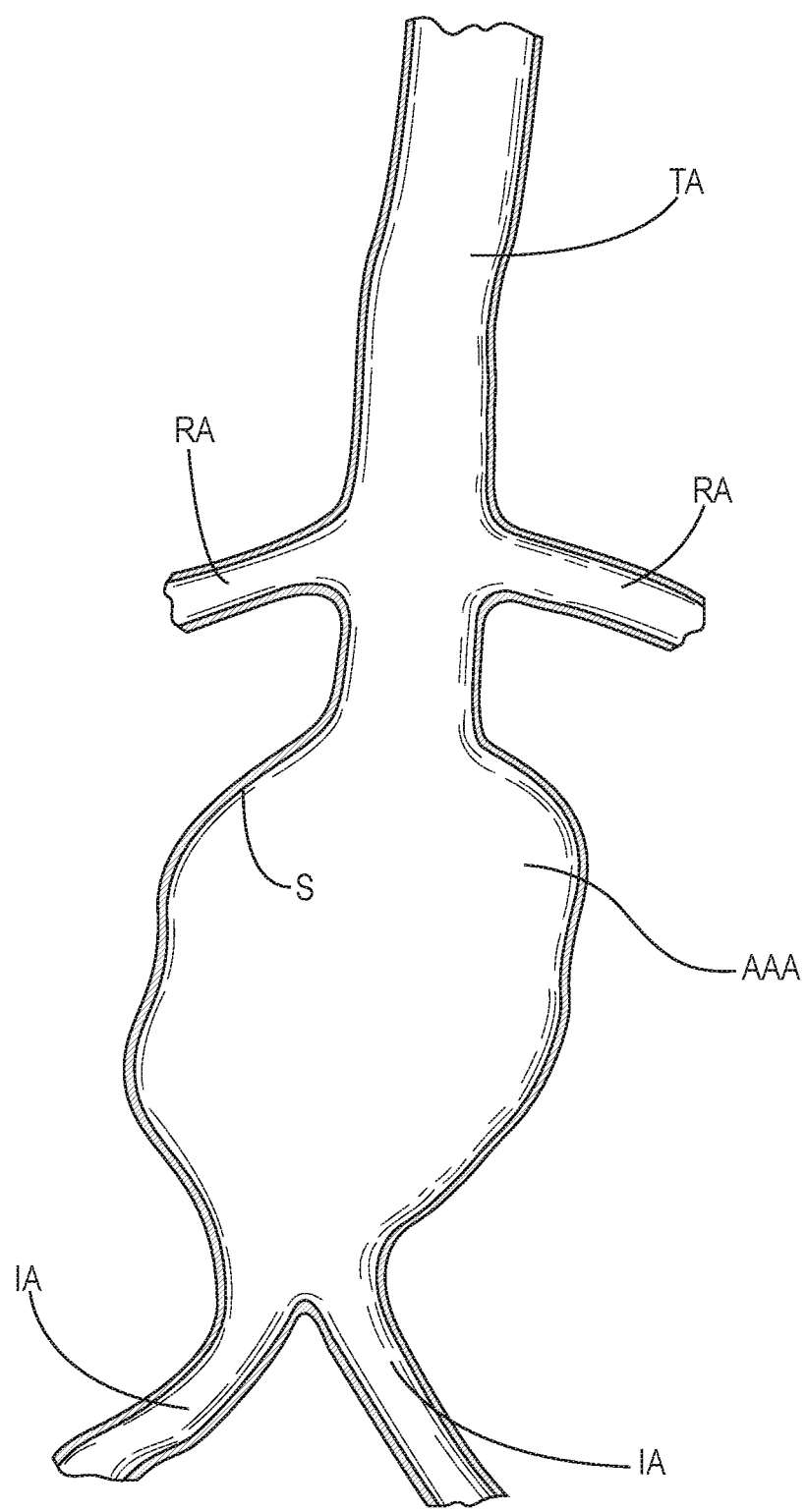
FIG. 2 is an illustration of the anatomy of an infrarenal abdominal aortic aneurysm.

FIG. 2 is an illustration of the anatomy of an infrarenal abdominal aortic aneurysm. The anatomy of an infrarenal abdominal aortic aneurysm comprises the thoracic aorta (TA) having renal arteries (RA) at its proximal end above the iliac arteries (IA). The abdominal aortic aneurysm (AAA) can form between the renal arteries (RA) and the iliac arteries (IA) and may have regions of mural thrombus over portions of its inner surface (S).

Figure 3:
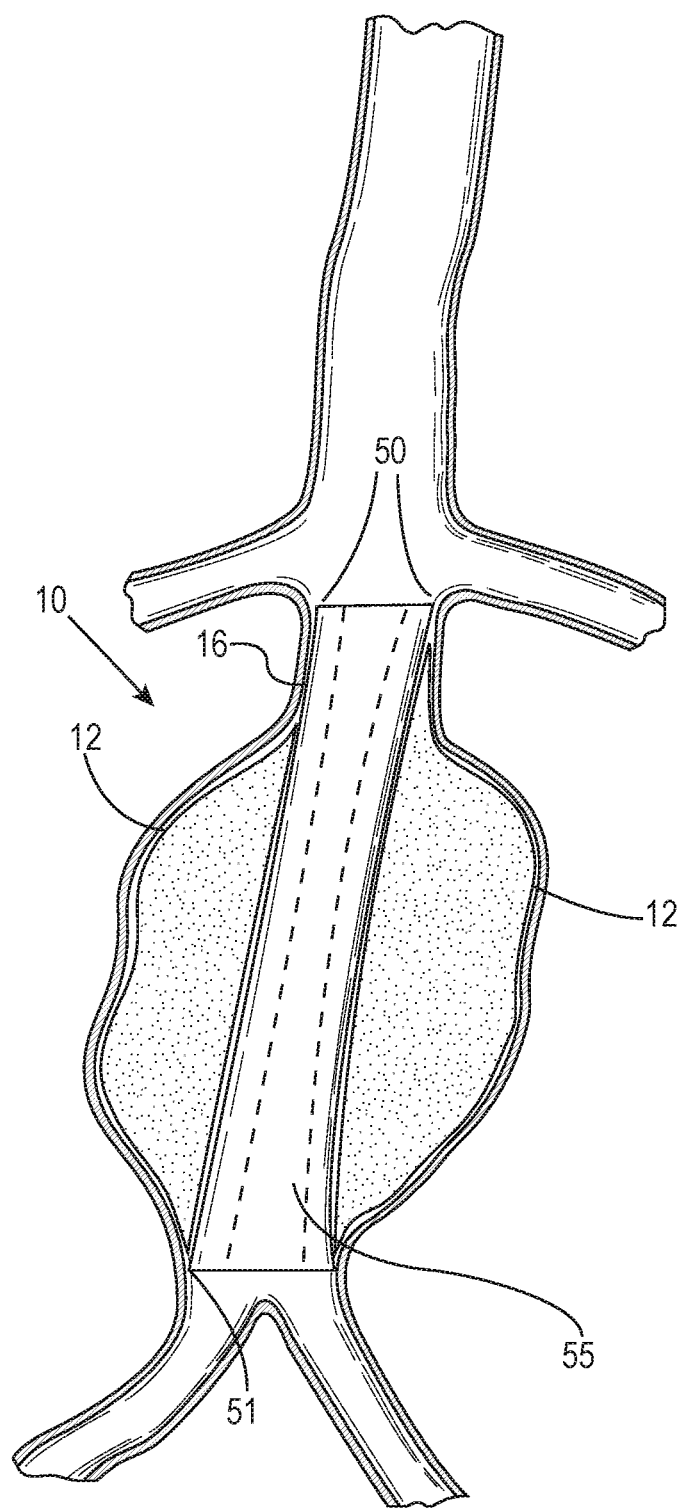
FIG. 3 is an illustration of a dual inflatable single prosthesis deployed within an aneurysm in accordance with an illustrative embodiment.

FIG. 3 is an illustration of a dual inflatable single prosthesis system 10 deployed within an aneurysm in accordance with an illustrative embodiment. While FIG. 3 illustrates the system 10 deployed within an infrarenal abdominal aortic aneurysm, the system 10 can be used in many other types of aneurysms. FIG. 3 is illustrative of the system 10 within an aneurysm, and is not limiting to the types of aneurysms or how the system 10 is used with an infrarenal abdominal aortic aneurysm. For example, the proximal end of the inner filling structure 16 can extend beyond one or both renal arteries. In another example, the distal end of the inner filling structure 16 can extend into either of the iliac arteries.

Inner filling structure 16 can produce a proximal seal 50 around an arterial wall and a distal seal 51 around an arterial wall. Within the interior wall of the inner filling structure 16 can be a lumen 55 defined by the dashed lines in FIG. 3. Inner filling structure 16, once inflated, can comprise a substantially straight lumen 55. With reference to FIGS. 1B, 2, and 3, the outer wall 38 of the inner filling structure 16 can be substantially straight through the aneurysm. The inner filling structure 16 can produce the proximal seal 50 and the distal seal 51 by being sufficiently pressed against the arterial wall. The pressure against the arterial wall by the inner filling structure 16 can be created by filling the internal space 34 of the inner filling structure 16 with a filling material to a sufficient pressure. The proximal seal 50 and distal seal 51 can be made on a portion of the arterial wall that is relatively strong and/or healthy. For example, the inner surface S of an AAA can be relatively weak. If the same pressure applied to form proximal seal 50 and distal seal 51 were applied to the inner surface S, the arterial wall could rupture. Accordingly, the inner filling structure 16 can be configured to only apply a sealing pressure against a portion of the arterial wall that is strong enough to have the pressure applied to the arterial wall without rupturing.

Similarly, the outer filling structure 12 can be configured to be inflated to a pressure that does not rupture the inner surface S. As such, the pressure within the inner filling structure 16 can be greater than the pressure within the outer filling structure 12 such that the proximal seal 55 and distal seal 51 are produced, but that the aneurysm is not ruptured.

The inner wall 36 and the outer wall 38 of the inner filling structure 16 can be configured such that, when filled, the inner filling structure 16 is non-conformative or fails to change shape beyond a certain point. That is, when filled to the sealing pressure, the inner filling structure 16 can form the lumen 55 that has substantially straight walls along the artery. Similarly, the outer wall 38 of the inner filling structure 16 can be substantially straight, and not conform to the shape of the aneurysm. For example, the inner wall 36 and the outer wall 38 can be made of material that can be expanded, but expands in a uniform manner along the length of the inner filling structure 16. In one embodiment, the material of the inner wall 36 and the outer wall 38 of the inner filling structure 16 can be the same. In another embodiment, the material of the inner wall 36 of the inner filling structure 16 can be different than the material of the outer wall 38 of the inner filling structure 16.

In an illustrative embodiment, the inner wall 36 of the inner filling structure 16 can comprise one or more circumferential restrictive elements. In an embodiment, the inner filling structure 16 can comprise several circumferential restrictive elements along the length of the inner wall 36 such that the inner filling structure 16 can be filled with a relatively high pressure but maintain a substantially straight inner wall 36 when inflated. The circumferential restrictive elements can be expandable. In an embodiment, the circumferential restrictive elements can be a first diameter when the inner filling structure 16 is uninflated and a second diameter when the inner filling structure 16 is inflated. In such an embodiment, the circumferential restrictive elements can be continuous along the circumference of the inner wall 36. That is, the circumferential restrictive elements can be disposed within the inner wall 36 in 360 degrees when the inner filling structure 16 is inflated and uninflated. The circumferential restrictive elements can be configured to define the lumen 55 to approximate the anatomy of a healthy artery. That is, the lumen 55 can be similar in shape and/or diameter as the artery would have if there was no aneurysm. The inner wall 36 of the inner filling structure 16 can further include a circumferential restrictive element that resists dilatation.

In an illustrative embodiment, the outer wall 38 of the inner filling structure 16 can comprise one or more circumferential restrictive elements. In an embodiment, the inner filling structure 16 can comprise several circumferential restrictive elements along the length of the outer wall 38 such that the inner filling structure 16 can be filled with a relatively high pressure but maintain a substantially straight outer wall 38 when inflated. The circumferential restrictive elements can be expandable. In an embodiment, the circumferential restrictive elements can be a first diameter when the inner filling structure 16 is uninflated and a second diameter when the inner filling structure 16 is inflated. In such an embodiment, the circumferential restrictive elements can be continuous along the circumference of the outer wall 38. That is, the circumferential restrictive elements can be disposed within the outer wall 38 in 360 degrees when the inner filling structure 16 is inflated and uninflated. The outer wall 38 of the inner filling structure 16 can further include a circumferential restrictive element that resists dilatation.

In embodiments with circumferential restrictive elements on either or both of the inner wall 36 of the inner filling structure 16 or the outer wall 38 of the inner filling structure 16, the circumferential restrictive elements can be disposed in equal distances along the entire inner filling structure 16. In other embodiments, the circumferential restrictive elements can be disposed along the inner filling structure 16 in only an inner portion of the inner filling structure 16 corresponding to the length of the aneurysm. In yet other embodiments, the circumferential restrictive elements can be disposed along either and/or both the proximal end or the distal end of the inner filling structure 16 corresponding to the healthy portion of the artery. Placing circumferential restrictive elements at the proximal end and the distal end of the inner filling structure 16 may prevent straightening of tortuous anatomy as a result of a concentric high pressure non-compliant filling structure's characteristic of longitudinal rigidity when inflated to higher pressures.

In some embodiments, the inner filling structure 16 can be configured to have an uninflated length that is similar or the same as an inflated length. That is, in various embodiments, when the inner filling structure 16 is inflated, the inner filling structure 16 can be configured to expand radially, but not longitudinally along the length of the inner filling structure 16.

In an embodiment of the present disclosure, the inner wall 36 and the outer wall 38 of the inner filling structure 16 can be comprised of a non-compliant plastic material. The plastic material can be any plastic material known in the art of angioplasty balloons. In other embodiments, the inner wall 36 and the outer wall 38 of the inner filling structure 16 can be comprised of a non-plastic material analogous to modern angioplasty balloons. In other embodiments, the inner filling structure 16 can be comprised of an aromatic polycarbonate (TPU) having a hardness of about 55D shore-A, an ultimate elongation of about 382, a tear-strength of about 781 lb/in, a tensile strength of about 7000 to 8000 UTS (i.e., 7848 UTS), a modulus of about 2170 (tensile@100%). Other embodiments of the inner filling structure 16 can include aromatic polycarbonate (TPU with 20% $BaSO_4$) having other properties like hardness of 56D shore-A, an ultimate elongation of about 2-350 (e.g, 25, 150, 200, 270, 275, 330, 350 and so on).

In some embodiments, the outer filling structure 12 can be comprised of compliant material that can expand to occupy the space within an aneurysm. In an example embodiment, the outer filling structure 12 may comprise aromatic polycarbonate (TPU) having a hardness of about 62 to 84 Shore-A (e.g., 70 or 77 shore-A) and modulus tensile at 100% of 500. Other properties of the outer filling structure 12 may include a tensile strength of 8000 and a modulus at tensile at 100% of 400, and a flexural modulus of about 1500.

In some embodiments, the outer filling structure 12 may comprise aromatic polyether (TPU) having a shore hardness of about 70 Shore-A, an ultimate elongation of 730, a tear-strength of 380 graves, a tear-strength of 110 trousers, and a tensile strength of 5300. In other embodiments, polyether (TPU) may be used for the outer filling structure 12.

As illustrated in FIG. 3, the lumen 55 can have a first diameter at the proximal end and a second diameter at the distal end. In some embodiments, the first diameter and the second diameter can be substantially similar. In other embodiments, such as the embodiment shown in FIG. 3, the first diameter can be smaller than the second diameter. In embodiments with circumferential restrictive elements, the circumferential restrictive elements can be configured to allow the diameter of the inner filling structure 16 to increase along the length of the inner filling structure 16 from the proximal end to the distal end. In such embodiments, the pressure exerted on the artery by the proximal seal 50 can be substantially similar to the pressure exerted on the artery by the distal seal 51. In other embodiments, the circumferential restrictive elements can be substantially similar along the length of the inner filling structure 16. In such embodiments, the difference in diameter along the inner filling structure 16 can be formed by a difference in pressure at the proximal seal 50 and the distal seal 51. That is, the proximal seal 50 can exert a higher pressure against the arterial wall than the distal seal 51. In such an embodiment, the inner filling structure 16 can comprise a semi-compliant material. That is, the inner filling structure 16 can comprise a material that allows the proximal end of the inner filling structure 16 to conform to the arterial wall at the proximal end and allow the distal end of the inner filling structure 16 to conform to the arterial wall of the distal end while maintaining a shape that does not extend to the inner wall S of the aneurysm. In other embodiments, the second diameter can be smaller than the first diameter.

In some embodiments, the inner filling structure 16 can form the lumen 55 that is 12 to 14 mm in diameter when inflated. In other embodiments, the inner filling structure 16 can form the lumen 55 that has a diameter greater or less than 12 to 14 mm. For example, the lumen 55 can have a diameter that is 11 mm, 10 mm, 9.5 mm, etc. or 15 mm, 16 mm, 16.5 mm, etc. With reference to FIGS. 1B, 2, and 3, when inflated in some embodiments, the internal space 34 of the inner filling structure 16, defined by the inner wall 36 and the outer wall 38, can be 3 to 4 mm radially. That is, a distance between the inner wall 36 and the outer wall 38 of the inner filling structure 16 can be 3 to 4 mm when inflated. In other embodiments, the distance between the inner wall 36 and the outer wall 38 of the inner filling structure 16 can be greater or less than 3 to 4 mm. For example, the distance between the inner wall 36 and the outer wall 38 of the inner filling structure 16 can be 2 mm, 1.5 mm, etc., or 5 mm, 5.5 mm, etc.

In an embodiment, the inner filling structure 16 can be configured to use stents to form the proximal seal 50 and/or the distal seal 51. In such embodiments, the ends of the inner filling structure 16 and the outer filling structure 12 can be configured to be disposed as close as possible to the stent. In some embodiments, stents can be comprised of a cobalt chrome alloy (CoCr). In some embodiments, stents can be comprised of a nickel titanium alloy (Nitinol).

In some embodiments, the inner filling structure 16 can be configured to not use stents to form the proximal seal 50 and the distal seal 51. In such embodiments, the inner filling structure 16 can extend beyond the aneurysm into a healthy portion of the artery to provide sufficient surface area within the healthy portion of the artery to provide a seal. In such embodiments, the proximal seal 50 can be sufficient to prevent blood from flowing from the proximal aorta into the aneurysmal sack. Similarly, the distal seal 51 can be sufficient to prevent blood from flowing through the lumen 55 back into the aneurysmal sack. Accordingly, in some embodiments, the proximal seal 50 can be stronger than the distal seal 51. In such embodiments, the inner filling structure 16 can extend beyond the proximal end of the outer filling structure 12 in a proximal direction by a first length, and extend beyond the distal end of the outer filling structure 12 in a distal direction by a second length. In some embodiments, the first length can be greater than the second length. In other embodiments, the first length can be less than or equal to the second length. In other embodiments, the proximal seal 50 can be as strong or stronger than the distal seal 51.

In an embodiment, the outer filling structure 12 can be comprised of a compliant material. In such an embodiment, the outer filling structure 12 can be a material that, when inflated, permits the inner wall 26 of the outer filling structure 12 to be defined by the outer wall 38 of the inner filling structure 16. Similarly, the outer wall 24 of the outer filling structure 12 can be defined by the inner surface S of the aneurysm. In an embodiment, the outer filling structure 12 can be comprised of a material that has similar properties to a latex balloon. In some embodiments, the outer filling structure 12 can be comprised of latex. In some embodiments, the outer filling structure 12 can be strong enough to not require redundancy or folding in the uninflated state or the inflated state. Further, the outer filling structure 12 can be smooth and act as a smooth outer surface of the sealing system.

In some embodiments, the inner filling structure 16 can be comprised of a material strong enough not to require the use of the outer filling structure 12 to act as a redundant force on the inner filling structure 16 to maintain a compliant shape. That is, the inner wall 26 of the outer filling structure 12 can comprise a material that is as compliant as the outer wall 24 of the outer filling structure 12. In other embodiments, the inner wall 26 can be a complaint material that can maintain its shape in the event that the inner filling structure 16 fails or deflates.

With reference to FIGS. 1A and 1B, in some embodiments, the outer filling structure 12 can be disposed around a portion of the inner filling structure 16, before inflation of the system 10, in a "stretched" state. That is, the inner filling structure 16 can have a first outer diameter when the inner filling structure 16 is disposed on the delivery catheter 14. The outer filling structure 12 can have a natural inner diameter that is a second diameter. The second diameter can be smaller than the first diameter. The natural inner diameter can be a diameter that the inner wall 26 of the outer filling structure 12 has when it is not disposed around the inner filling structure 16. The outer filling structure 12 can then be stretched around the inner filling structure 16, disposed on the delivery catheter 14, such that the inner diameter of the outer filling structure 12 is substantially similar to the outer diameter of the inner filling structure 16. In other embodiments, the natural inner diameter of the inner wall 26 of the outer filling structure 12 (the second diameter) can be substantially similar to the outer diameter of the inner filling structure 16 such that the outer filling structure 12 requires minimal (or no) stretching to be disposed around the inner filling structure 16.

Figure 4:
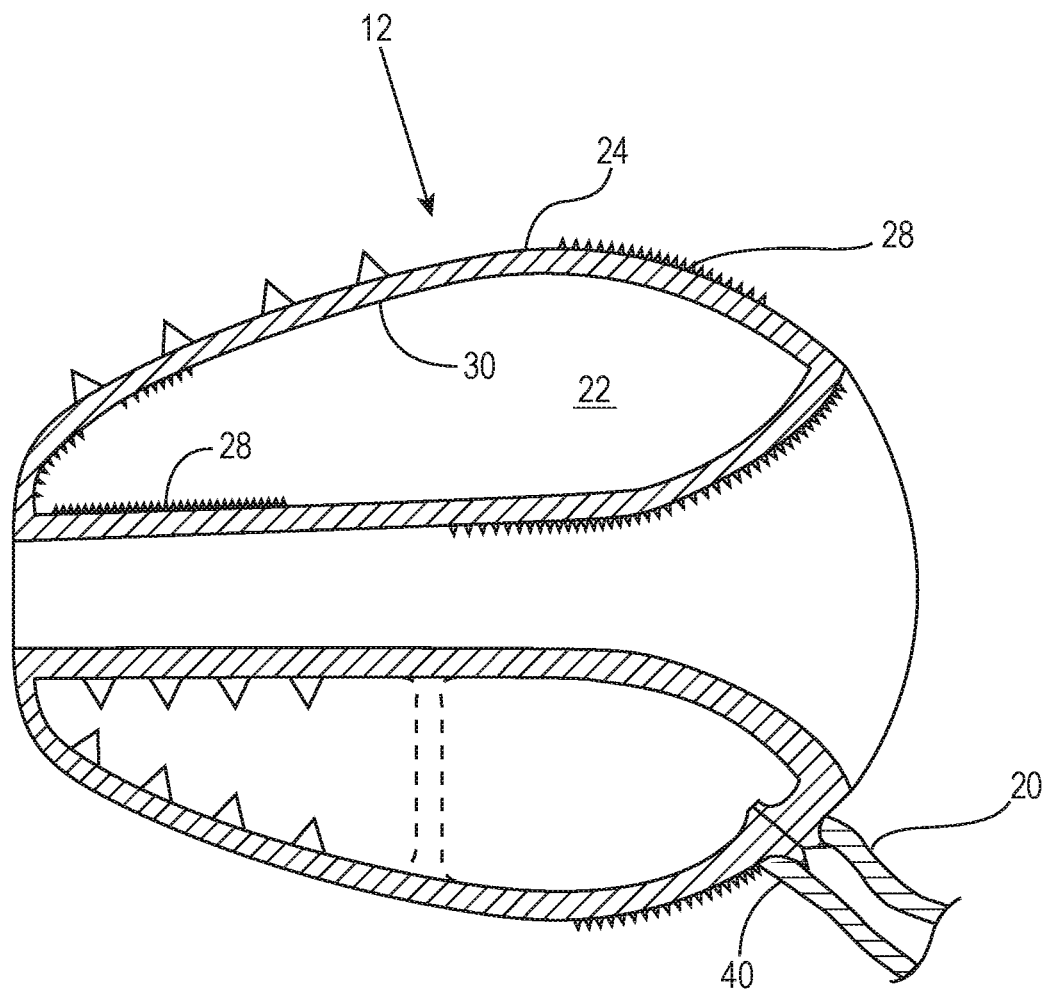
FIG. 4 is a cross-sectional view of a filling structure of FIG. 1A illustrating various surface modifications and a filling valve in accordance with an illustrative embodiment.

Referring now to FIG. 4, the various internal and external surfaces may be shaped, coated, treated, or otherwise modified, to provide for a number of features in accordance with the principles of the present disclosure. In some embodiments, a wall of a filling structure may be shaped to have rings, stipples, hook and loop, small barbs, or other surface features which can be formed into the material of the filling structure at the time of molding, vapor deposition, or other manufacturing process. The surface of the filling structure may also be coated with materials 28 which can be adhesives, drugs, active substances, fibers, flocking, foams, or a variety of other materials. A material that coats a surface of the filling structure can be biocompatible and/or biodegradable. With reference to FIGS. 1B, 2, and 4, in some embodiments, such surface features or modifications can be configured to enhance sealing or attachment of the outer wall 24 of the outer filling structure 12 to the inner surface S of the aneurysm being treated. In some embodiments, such surface features or modifications may be configured to enhance sealing or attachment of the inner filling structure 16 to the arterial wall. In some embodiments, such surface features or modifications may be configured to enhance sealing or attachment of the inner filling structure 16 and the outer filling structure 12.

The inner surface 30 of the internal space 22 of the outer filling structure 12, or the internal space 34 of the inner filling structure 16, may be modified by providing features, coatings, surface roughening, or a variety of other modifications. The purpose of such internal features can be to enhance adherence of the walls to the filling material or medium as the medium is cured or otherwise hardened. In some embodiments, materials may be coated on all or a portion of the inner surface 30 to induce or catalyze hardening of the filling material as it is being introduced.

The outer filling structure 12, or the inner filling structure 16, can comprise at least one valve 40 to permit the introduction of the filling material or medium into the internal space 22 of the outer filling structure 12 or the internal space 34 of the inner filling structure 16. As illustrated, the valve 40 can be a simple flap valve. Ball valves or one-way valve structures can be used. In some embodiments, two-way valve structures may be provided to permit both filling and selective emptying of the internal space 22 of the outer filling structure 12 or the internal space 34 of the inner filling structure 16. In some embodiments, the filling tube can comprise a needle or other filling structure to pass through the valve 40 to permit both filling and removal of filling medium.

Figure 6A:
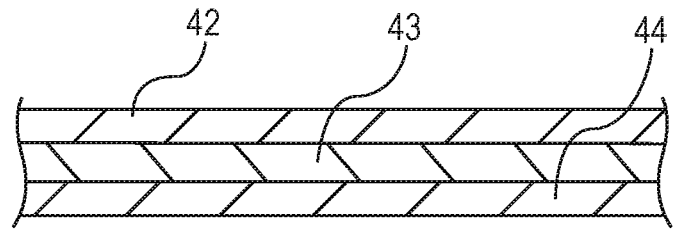
FIGS. 6A, 6B, and 6C illustrate alternative wall structures for a filling structure in accordance with illustrative embodiments.
Figure 6B:
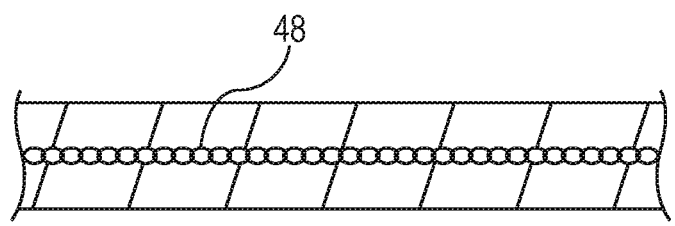
Figure 6C:
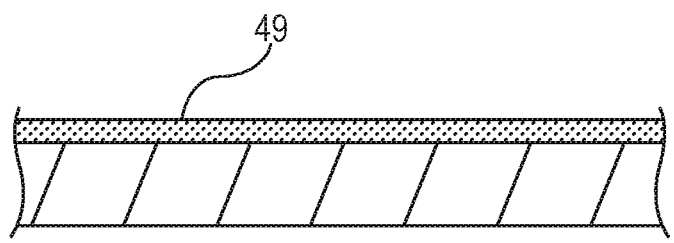

As illustrated in FIG. 4, the wall structure of the filling structure may be a single layer that can be molded or otherwise conventionally formed. The wall structures may also be more complex, as illustrated, for example, in FIGS. 6A, 6B, and 6C. FIG. 6A illustrates a multi-layered wall comprising layers 42, 43 and 44. It will be appreciated that such multiple layer structure can provide for increased strength, puncture resistance, variations in compliance and/or flexibility, differences in resistance to degradation, or other desired features. As shown in FIG. 6B, a single wall or multiple wall structure can be reinforced by braid 48, coils, or other metal or non-polymeric reinforcement layers or structures. As shown in FIG. 6C, an external surface 49 of the wall may be covered with drugs, fibers, protrusions, holes, active agents or other substances for a variety of purposes.

With reference to FIGS. 1A, 1B, and 4, in some embodiments, an adherent substance or a mechanical alteration of the surface can be disposed on an outer surface of the inner filling structure 16, the inner surface of the outer filling structure 12, or both. Such adherent substance or mechanical alteration can provide a sealing system or an adherent system such that the outer filling structure 12 is maintained in a position relative to the inner filling structure 16 while the outer filling structure 12 is inflated. The adherent substance or mechanical alteration can be configured such that any sealing system or adherent system breaks down and no longer seals the outer filling structure 12 and the inner filling structure 16 if the outer filling structure 12 is deflated. Such an adherent substance or mechanical alteration can allow for removal of the outer filling structure 12 without removal of the inner filling structure 16.

In some embodiments, a graft can be used with system 10. In some embodiments, the graft can help to maintain a shape of the lumen 55. The graft can help to prevent the lumen 55 from becoming dilated or from collapsing. In some embodiments, the graft can serve as a biocompatible blood interface. A graft can be used regardless of whether the inner filling structure 16 is capable of maintaining a shape on its own. In some embodiments, the graft can help provide structural support. In other embodiments, the graft can be for a biocompatible blood interface and not provide significant structural support. In some embodiments, grafts can be comprised of expanded polytetrafluoroethylene (ePTFE) or similar materials.

System 10 can be used with a stent. In some embodiments, a biolimus-eluting stent can be used with the system 10. In some embodiments, a sirolimus-eluting stent can be used with the system 10. The stent can be used to seal the lumen 55 and the arterial wall to prevent blood from entering the aneurysmal sack. If a stent is used to seal the system, then the stent can be mounted, for example, on bare angioplasty balloons that are 12 to 14 mm in diameter. In other embodiments, the stent can be mounted on bare angioplasty balloons that are greater than or less than 12 to 14 mm in diameter. If a stent is used, it can be disposed, for example, on the delivery catheter 14 and deployed with the system 10. In some embodiments, the system 10 can be deployed and one or more stents can be introduced after the system 10 is in place. A stent can be used on a proximal end of the system 10, a distal end of the system 10, or both. In some embodiments, an inner diameter of the stent can be 12 to 14 mm. In other embodiments, the stent can have an inner diameter of less than or greater than 12 to 14 mm.

Figure 5A:
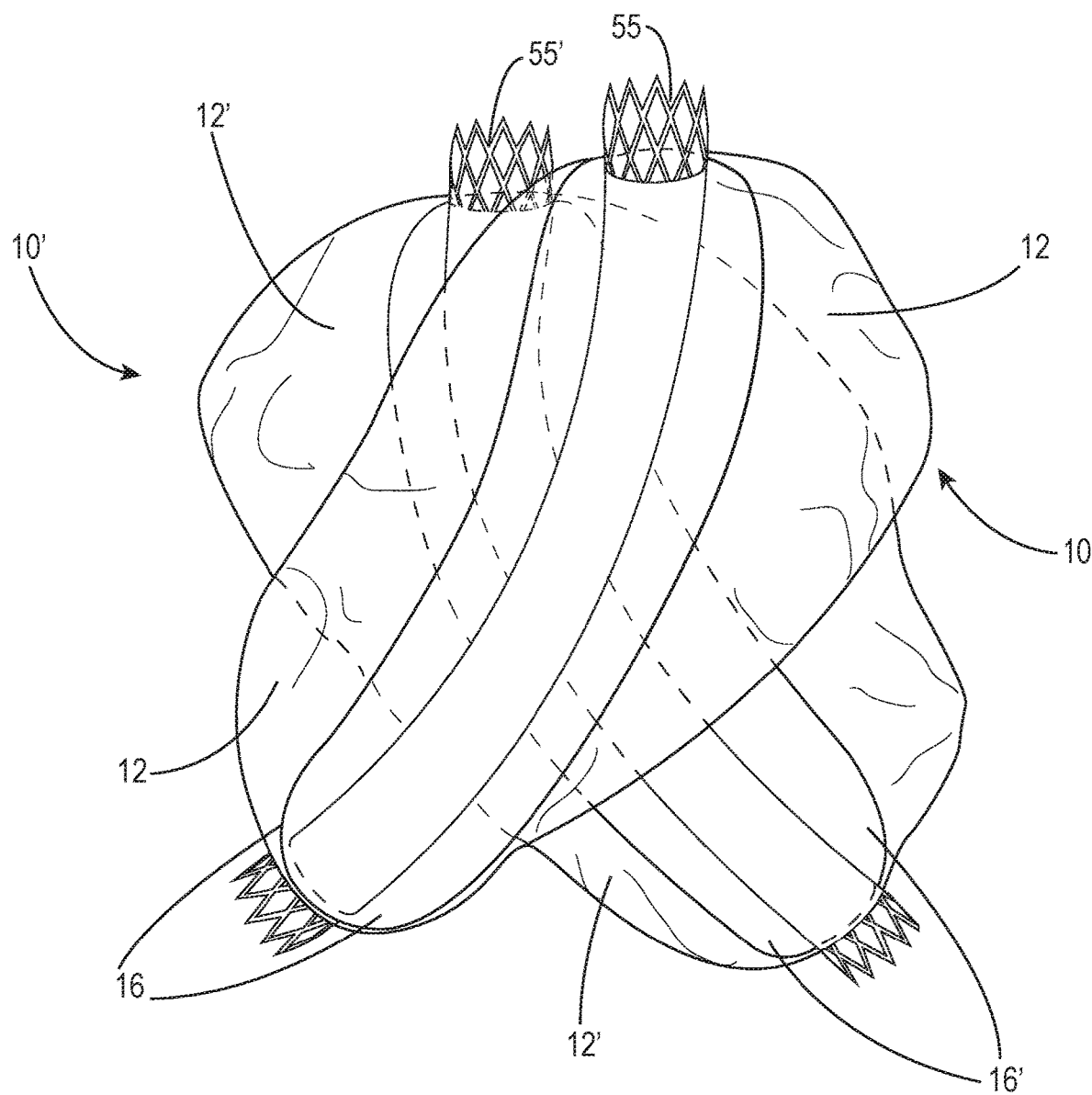
FIGS. 5A and 5B are an illustration of a dual inflatable dual prosthesis in accordance with an illustrative embodiment.
Figure 5B:
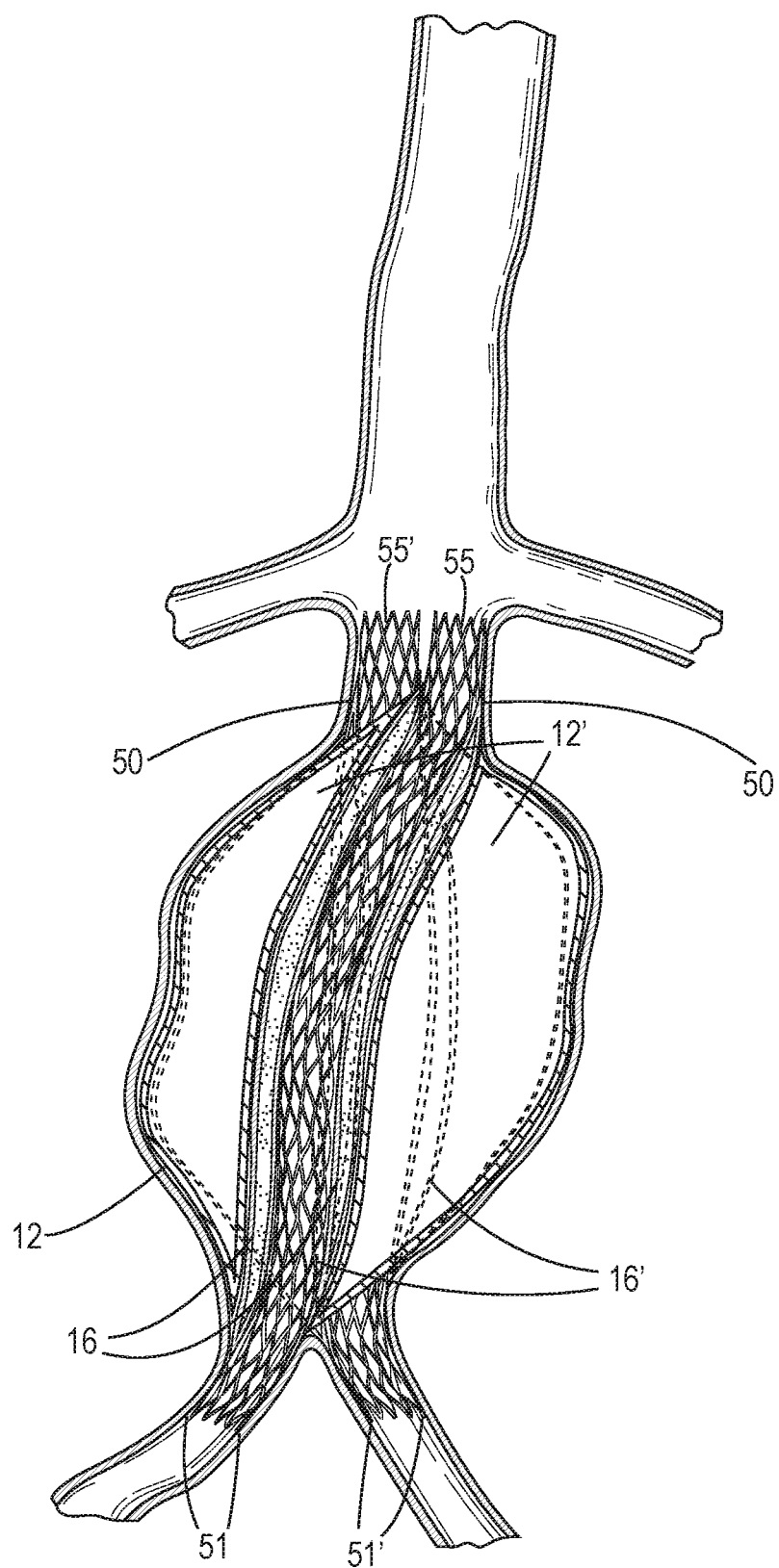

FIG. 5A is an illustration of a dual inflatable dual prosthesis system including the system 10 and a system 10' in a deployed state in accordance with an illustrative embodiment. The system 10' is similar to the system 10, and like numerals indicate like elements of the systems, where the numerals for the elements of the system 10' are followed by a "'" symbol in the figures. FIG. 5B is an illustration of a dual inflatable dual prosthesis system including the system 10 and the system 10' of FIG. 5A deployed within an aneurysm in accordance with an illustrative embodiment. With reference to FIGS. 5A and 5B, while FIG. 5B illustrates two systems 10, 10' deployed within an infrarenal abdominal aortic aneurysm, systems 10, 10' can be used in many other types of aneurysms. FIG. 5B is illustrative of systems 10, 10' of FIG. 5A within an aneurysm, and is not limiting to the types of aneurysms or how systems 10, 10' are used with an infrarenal abdominal aortic aneurysm. For example, the proximal end of inner filling structures 16 and 16' can extend beyond one or both renal arteries. In another example, the distal end of the inner filling structures 16 and 16' can terminate before either or both of the iliac arteries.

With reference to FIGS. 5A and 5B, two systems 10, 10' can be used within an aneurysm. The lumens 55 and 55' can be used together to approximate a healthy artery system within an aneurysm. Together, the inner filling structures 16 and 16' can form a proximal seal 50 within a relatively healthy part of the artery. The inner filling structure 16 can form a distal seal 51 within an iliac artery. The inner filling structure 16' can form a distal seal 51' within another iliac artery. Alternatively, the inner filling structures 16 and 16' can be configured to not form a seal within the iliac arteries and can form a seal similar to the seal 51 in FIG. 3. The outer filling structures 12 and 12' can fill an area of the aneurysm between the inner filling structures 16 and 16' and the inner surface of the aneurysm. Additionally, the outer filling structures 12 and 12' can fill the space between the inner filling structure 16 and the inner filling structure 16'.

The outer filling structures 12 and 12' can be compliant, as discussed above with reference to FIG. 3, while still being flexible to conform to the shape of the arteries.

Figure 7:
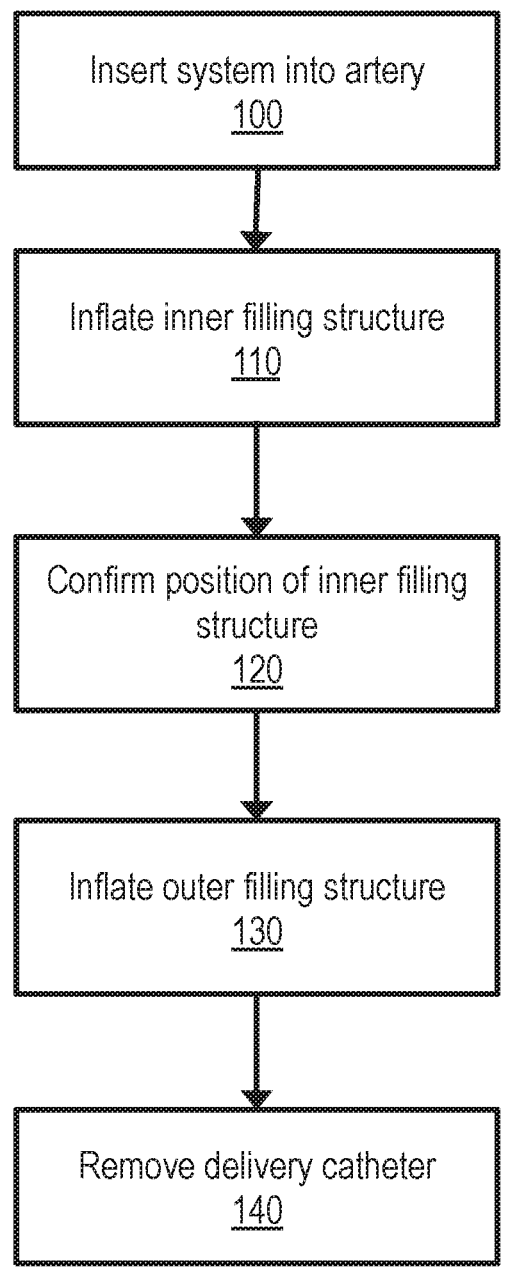
FIG. 7 is a flowchart of a method of deploying a dual inflatable single prosthesis in accordance with an illustrative embodiment.

FIG. 7 is a flowchart of a method of deploying a dual inflatable single prosthesis system in accordance with an illustrative embodiment. In alternative embodiments, fewer, additional, and/or different operations may be performed. Also, the use of a flowchart is not meant to be limiting with respect to the order of operations performed.

With reference to FIGS. 1A, 1B, 2, 3, and 7, step 100 comprises inserting the system 10 into an artery. Inserting system 10 into an artery can include inserting a guidewire into the circulatory system. The delivery catheter 14 can be inserted into a desired position by sliding the delivery catheter 14 over the guidewire.

Step 110 comprises inflating the inner filling structure 16. The material used to fill the inner filling structure 16 can be any desired material for inflating. In an embodiment, the filling material can be a material that cures to a hardened state. In other embodiments, the filling material can remain in a fluid state and the material of the inner wall 36 and the material of the outer wall 38 can be sufficiently rigid to maintain a desired shape of the inner filling structure 16. Inflating the inner filling structure 16 can include filling the inner filling structure 16 to a desired pressure.

Step 120 comprises confirming a position of the inner filling structure 16. In various embodiments, imaging is used to determine the position of a prosthesis within a circulatory system. Confirming the position of the inner filling structure 16 can include confirming that a seal is made. A determination can be made that the inner filling structure 16 has produced a sufficient proximal seal 50. A determination can be made that the inner filling structure 16 has produced a sufficient distal seal 51. A pressure reading of a pressure inside of the inner filling structure 16 can be taken. A pressure reading above a sealing pressure threshold can be used to determine that inner filling structure 16 has produced a seal. The pressure reading in combination with an image showing that the inner filling structure 16 is within a relatively healthy portion of the artery (at either and/or both the proximal end and the distal end) can be used to determine that the inner filling structure 16 has produced a seal. A pressure reading above a rupture pressure threshold can be used to determine that the inner filling structure 16 has been over-pressured and is in danger of rupturing. Step 120 can be before or after the material used to fill the inner filling structure 16 has cured.

In some embodiments, inflating the inner filling structure 16 can be completed prior to inflating the outer filling structure 12. Such a sequence can help to stabilize the system 10 at a relatively early stage of the procedure. As such, treatment of both intact and ruptured aneurysms can be facilitated. Further, positioning of the proximal and distal ends of the sealing system can be facilitated by such a sequence. Additionally, maintenance of the position (e.g., Step 120) through the completion of the procedure (including Step 130) can be facilitated. Maintenance of the position while inflating the outer filling structure 12 can especially be facilitated if the inner filling structure 16 is fully cured before the outer filling structure 12 is inflated.

Step 130 comprises inflating the outer filling structure 12. The material used to fill the outer filling structure 12 can be any desired material for inflating. In an embodiment, the filling material can be a material that cures to a hardened state. In other embodiments, the filling material can remain in a fluid state and the material of the inner wall 26 can be sufficiently rigid to maintain a desired shape of the outer filling structure 12. Inflating the outer filling structure 12 can include filling the outer filling structure 12 to a desired pressure. The desired pressure can be determined based on the purpose of inflating the outer filling structure 12. In an embodiment, inflating the outer filling structure 12 can be used to obliterate or rupture a sack of liquid blood within the aneurysm. In an embodiment, inflating the outer filling structure can be used to occupy space between the inner filling structure 16 and the inner surface S of the aneurysm. Accordingly, the desired pressure can be determined to be below a pressure that would rupture the wall of the aneurysm. In some embodiments, a pressure within the outer filling structure 12 is less than a pressure within the inner filling structure 16. In some embodiments, Step 130 can be simultaneous to Step 110. In such embodiments, Step 120 can be simultaneous to Steps 130 and 110, or can be performed after Steps 130 and 110.

Step 140 can include removing the delivery catheter 14. In some embodiments, a filling lumen used to inflate either and/or both the inner filling structure 16 and the outer filling structure 12 can be removed from the respective filling structures. Removing the filling lumen can include ensuring that a filling hole of the filling structure is closed and does not allow filling material to escape from the filling structure. Removing the filling lumen can be done in an order different than that shown in FIG. 7. For example, removing a filling lumen used to inflate the inner filling structure 16 can be done before filling the outer filling structure 12. In an embodiment, removing the filling lumen from the inner filling structure 16 can be done prior to confirming the position of the inner filling structure 16. The delivery catheter 14 can also be removed from the circulatory system.

Figure 8:
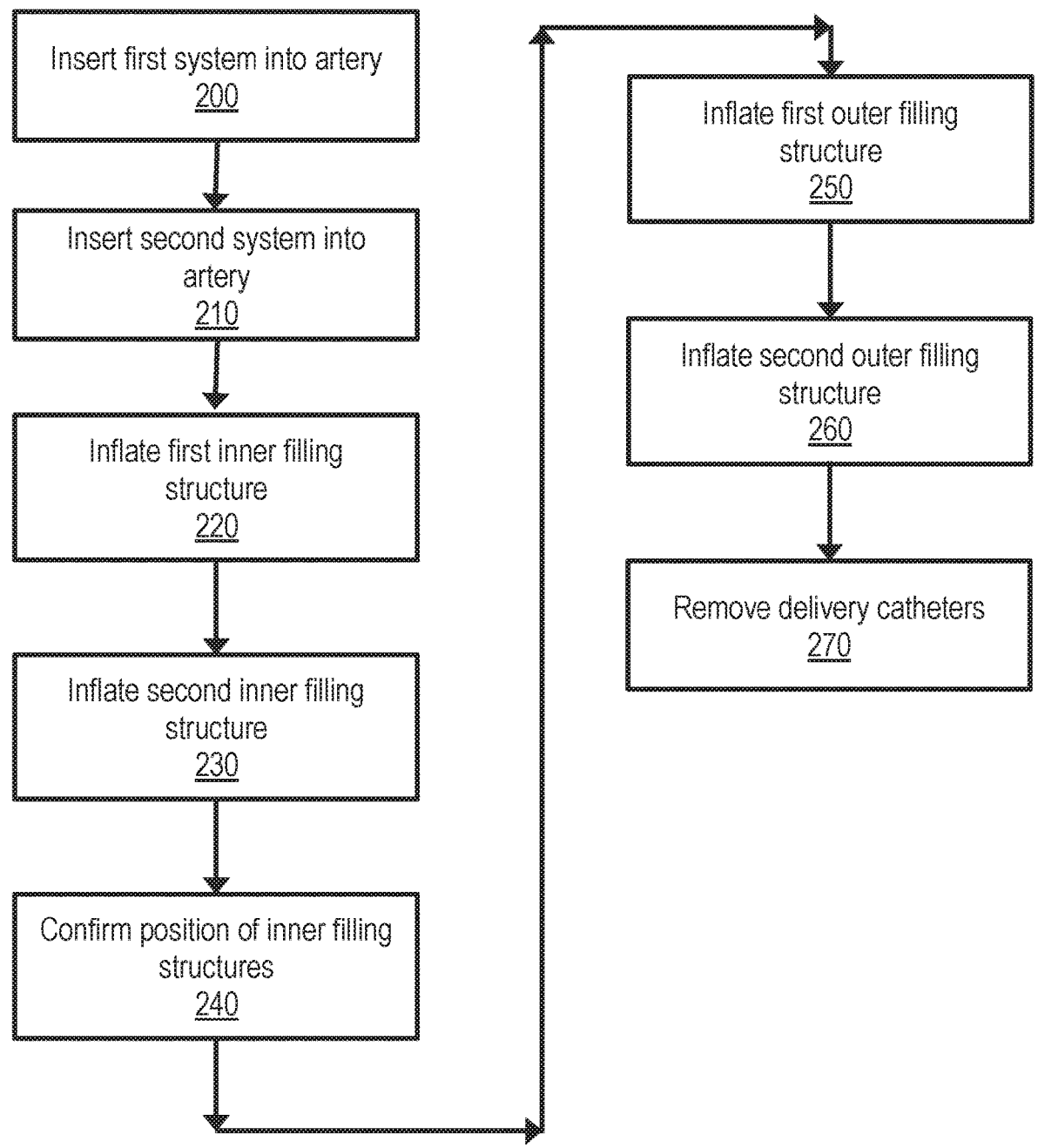
FIG. 8 is a flowchart of a method of deploying a dual inflatable dual prosthesis in accordance with an illustrative embodiment.

FIG. 8 is a flowchart of a method of deploying a dual inflatable dual prosthesis system in accordance with an illustrative embodiment. In alternative embodiments, fewer, additional, and/or different operations may be performed. Also, the use of a flowchart is not meant to be limiting with respect to the order of operations performed.

With reference to FIGS. 1A, 1B, 5A, 5B, and 8, step 200 comprises inserting the system 10 into an artery. Inserting the system 10 into an artery can include inserting a first guidewire into the circulatory system. The delivery catheter 14 can be inserted into a desired position by sliding the delivery catheter 14 over the first guidewire.

Step 210 comprises inserting the system 10' into an artery. Inserting the system 10' into an artery can include inserting a second guidewire into the circulatory system. A second delivery catheter can be inserted into a desired position by sliding the second delivery catheter over the second guidewire.

Step 220 comprises inflating the inner filling structure 16. The material used to fill first inner filling structure 16 can be any desired material for inflating. In an embodiment, the filling material can be a material that cures to a hardened state. In other embodiments, the filling material can remain in a fluid state and the material of the inner wall 36 and the material of the outer wall 38 can be sufficiently rigid to maintain a desired shape of the inner filling structure 16. Inflating the inner filling structure 16 can include filling the inner filling structure 16 to a first desired pressure.

Step 230 comprises inflating the inner filling structure 16'. The material used to fill the inner filling structure 16' can be any desired material for inflating. In an embodiment, the filling material can be a material that cures to a hardened state. In other embodiments, the filling material can remain in a fluid state and the material of the inner wall and the material of the outer wall of the inner filling structure 16' can be sufficiently rigid to maintain a desired shape of the inner filling structure 16'. Inflating the inner filling structure 16' can include filling the inner filling structure 16' to a second desired pressure. The first pressure and the second pressure can be the same or different. Step 220 and Step 230 can be performed simultaneously.

Step 240 comprises confirming a position of the inner filling structure 16 and the inner filling structure 16'. Imaging can be used to determine the positions. Confirming the position of the inner filling structure 16 and the inner filling structure 16' can include confirming that a seal is made. A determination can be made that the inner filling structure 16 and the inner filling structure 16' have produced a sufficient proximal seal 50. A determination can be made that the inner filling structure 16 has produced a sufficient distal seal 51. A determination can be made that the inner filling structure 16' has produced a sufficient distal seal 51'. In some embodiments, a determination can be made that the inner filling structure 16 and the inner filling structure 16' have produced a sufficient distal seal together. Pressure readings of a pressure inside of the inner filling structure 16 and the inner filling structure 16' can be taken. Pressure readings above a sealing pressure threshold can be used to determine that the inner filling structure 16 and the inner filling structure 16' have produced a seal. The pressure readings in combination with an image showing that the inner filling structure 16 and the inner filling structure 16' are within a relatively healthy portion of the artery (at either and/or both the proximal end and the distal end) can be used to determine that the inner filling structure 16 and the inner filling structure 16' have produced a seal. A pressure reading above a rupture pressure threshold can be used to determine that the inner filling structure 16 or the inner filling structure 16' have been over-pressured and are in danger of rupturing. Step 240 can be before or after the material used to fill the inner filling structure 16 and the inner filling structure 16' has cured.

Step 250 comprises inflating the outer filling structure 12. The material used to fill the outer filling structure 12 can be any desired material for inflating. In an embodiment, the filling material can be a material that cures to a hardened state. In other embodiments, the filling material can remain in a fluid state and the material of the inner wall 26 can be sufficiently rigid to maintain a desired shape of the inner filling structure 16. Inflating the outer filling structure 12 can include filling the outer filling structure 12 to a desired pressure. The desired pressure can be determined based on the purpose of inflating the outer filling structure 12. In an embodiment, inflating the outer filling structure 12 can be used to obliterate or rupture a sack of liquid blood within the aneurysm. In an embodiment, inflating the outer filling structure 12 can be used to occupy space between the inner filling structure 16 and a portion of the inner surface of the aneurysm. Accordingly, the desired pressure can be determined to be below a pressure that would rupture the wall of the aneurysm. In an embodiment, inflating the outer filling structure 12 can be used to occupy space between the inner filling structure 16 and the outer filling structure 12'.

Step 260 comprises inflating the outer filling structure 12'. The material used to fill the outer filling structure 12' can be any desired material for inflating. In an embodiment, the filling material can be a material that cures to a hardened state. In other embodiments, the filling material can remain in a fluid state and the material of the inner wall of the outer filling structure 12' can be sufficiently rigid to maintain a desired shape of the inner filling structure 16'. Inflating the outer filling structure 12' can include filling the outer filling structure 12' to a desired pressure. The desired pressure can be determined based on the purpose of inflating the outer filling structure 12'. In an embodiment, inflating the outer filling structure 12' can be used to obliterate or rupture a sack of liquid blood within the aneurysm. In an embodiment, inflating the outer filling structure 12' can be used to occupy space between the inner filling structure 16' and a portion of the inner surface of the aneurysm. Accordingly, the desired pressure can be determined to be below a pressure that would rupture the wall of the aneurysm. In an embodiment, inflating the outer filling structure 12' can be used to occupy space between the inner filling structure 16' and the outer filling structure 12. In some embodiments Step 250 and Step 260 can be simultaneous. In yet further embodiments, Steps 220, 230, 250, and 260 can be simultaneous. In such embodiments, Step 240 can be simultaneous to Steps 220, 230, 240, and 250, or can be performed after Steps 220, 230, 240, and 250.

Step 270 can include removing the delivery catheters, such as the delivery catheter 14 for the system 10 and a delivery catheter for the system 10'. A filling lumen used to inflate either and/or both the inner filling structure 16 and the outer filling structure 12 can be removed from the respective filling structures. A filling lumen used to inflate either and/or both the inner filling structure 16' and the outer filling structure 12' can be removed from the respective filling structures. Removing the filling lumen can include ensuring that a filling hole of the filling structure is closed and does not allow filling material to escape from the filling structure. Removing the filling lumen can be done in an order different than that shown in FIG. 8. For example, removing a filling lumen used to inflate the inner filling structure 16 can be done before filling the outer filling structure 12. In an embodiment, removing the filling lumen from the inner filling structure 16 can be done prior to confirming the position of the inner filling structure 16.

An aorto-iliac tube dual pressure system having a dual compliance sealing system may provide proximal and distal treatment. Two devices or two lumen treatment of aorto-iliac disease allows for treatment of aortic disease where each device can be extended to a patient iliac lumen. Alternative use as a single device/single lumen treatment for anatomy and disease states that clinical decision making dictates an aorto-uniiliac reconstruction. The stent used in the device may be, for example, a biolimus-eluting stent (BES) or sirolimus-eluting stent (SES). The stents may be a component of the sealing system or delivered secondarily after the sealing system is in place. Stent diameters that optimize the luminal diameter and the sealing of the system would be utilized. For example, 12 or 14 mm inner diameter lumens are envisioned but the design is not limited to these diameters or to a variation of diameter. The BES or SES could be covered with a graft material as well delivered either coincident or secondarily after placement of the sealing system.

In some embodiments, the lumen supporting stent is not integral to the sealing system. In those embodiments, the sealing system could be mounted on bare angioplasty balloons that are approximately 12 to 14 mm in diameter. The angioplasty balloons used to form or support lumens during deployment can have a length sufficient to support the lumens or a length that extends proximally well beyond the lumens as a way to provide improved proximal device orientation to the proximal aorta. The angioplasty balloons may be utilized to primarily form the lumen of the sealing system either with a stent or without a stent. In various embodiments, the system may incorporate a design with a circumferentially restrictive element on the outer diameter that would allow the balloon to be filled to higher pressure while retaining a shape consistent with the luminal course of the native anatomy (i.e. this feature would prevent "straightening" of tortuous anatomy as a result of a concentric high pressure non-compliant balloon's characteristic of longitudinal rigidity when inflated to higher pressures).

In various embodiments, the sealing system may include an inner bag with an approximately 12 to 14 mm in diameter open central lumen. Luminal diameter might be different than a 12 to 14 mm diameter or of varying diameter such as but not limited to, 8 mm, 8.5 mm, 9 mm, 9.5 mm, 10 mm, 10.5 mm, 11 mm, 11.5 mm, 12 mm, 12.5 mm, 13 mm, 13.5 mm, 14 mm, 14.5 mm, 15 mm, etc. The luminal diameter may be adjustable in situ when the system is inserted into the aorta. In various embodiments, the inner bag's central wall to lateral wall distance may be variable but in some embodiments it may be approximately in a range of 3 to 4 mm. However, in other embodiments, the inner bag central wall to lateral wall distance may be 2 mm, 2.5 mm, 3 mm, 3.5 mm, 4 mm, 4.5 mm, 5 mm, or 5.5 mm. In various embodiments, the inner bag is of a non-compliant plastic material with properties that may be similar to modern angioplasty balloons. The inner bag would be intended to originate and terminate as close to the proximal and distal ends of the stent as possible in embodiments that incorporate the stent into the sealing system.

Figure 9:
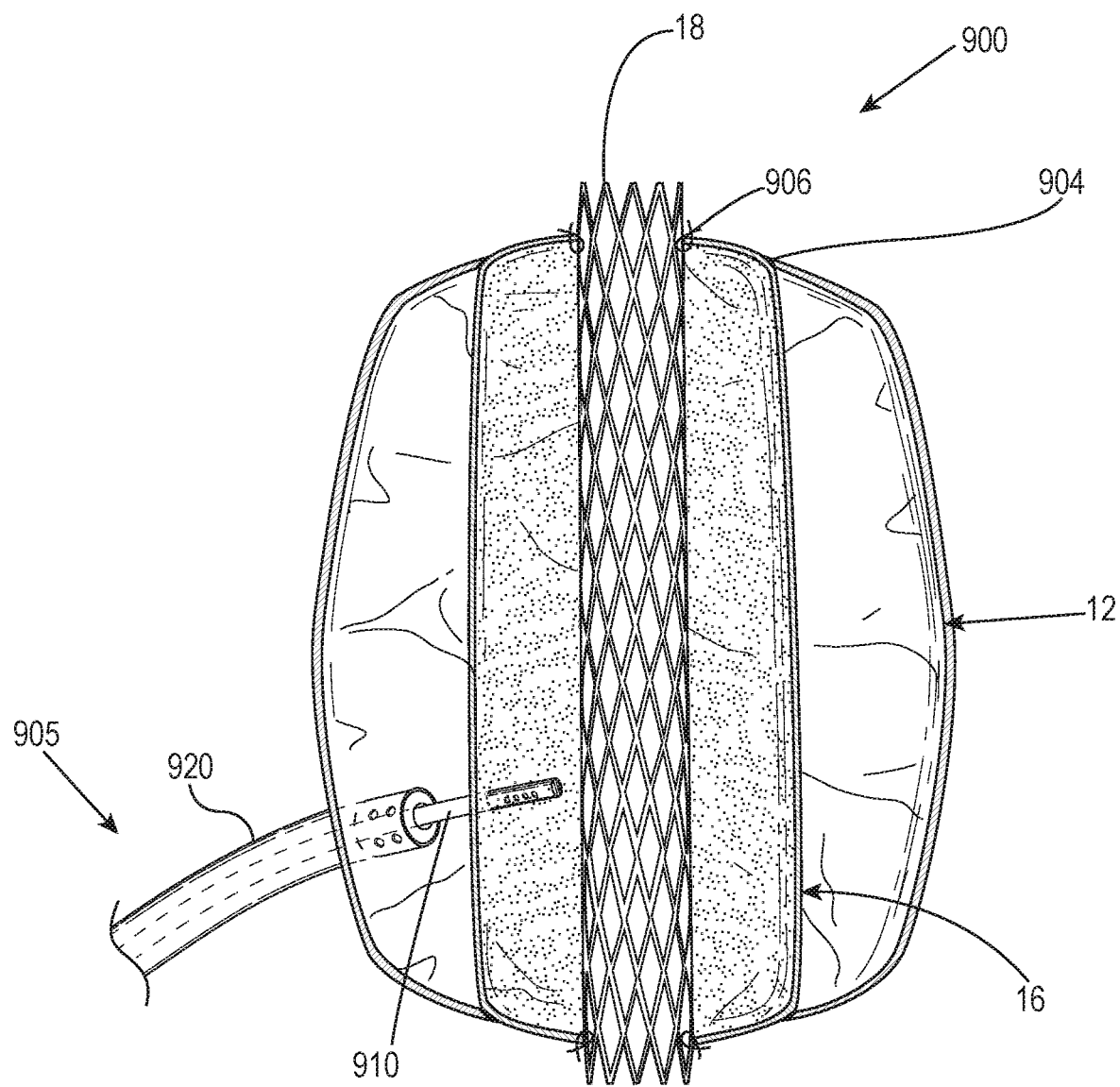
FIG. 9 is an illustration of a dual inflatable single prosthesis in accordance with an illustrative embodiment.

FIG. 9 illustrates another embodiment of a dual inflatable prosthesis 900. In various embodiments, the inflatable prosthesis 900 includes an outer filling structure 12 and an inner filling structure 16, a stent 18, and a fill line 905. The dual inflatable prosthesis 900 may operate in a similar manner as with the system of FIG. 1B and the processes described in FIGS. 7 and 8. In some embodiments, the dual inflatable prosthesis 900 may be manufactured without a stent 18 and the inner filling structure 16 may be used to create a lumen and a bridge across an aneurysm from a healthy proximal region to a healthy distal region of the aorta.

In the embodiment shown in FIG. 9, the inner filling structure 16 may be attached to the stent 18 using one or more sutures 906 at both ends of the stent 18. In other embodiments, a proximal portion of the inner filling structure 16 may be attached to a proximal portion of the stent 18. In various embodiments, a distal portion of the inner filling structure 16 may be detached or attached to a distal portion of the stent 18. As shown in FIG. 9, the outer filling structure 12 may be attached to an outer surface of the inner filling structure 16. In some embodiments, the attachment 904 may be distal to the attachment suture 906. In other embodiments, the attachment 904 may be at the same height relative to the stent 18. The attachment 904 between the outer filling structure 12 and the inner filling structure 16 may be created using heat bonding, glue bonding, welding, sutures or other suitable attachment mechanism.

Also shown in FIG. 9 is the fill line 905. In some embodiments, the fill line 905 comprises an inner fill line 910 and an outer fill line 920. The fill line 905 may be a concentric line. For example, the inner fill line 910 may be used for transport of a hardenable liquid into the inner filling structure 16. As discussed above, the inner filling structure 16 may be filled with a hydrogel material that is at a different pressure than deep pressure of the blood flowing through the stent 18. In some embodiments, the inner filling structure 16 may be filled to a pressure three or four times the pressure of the blood flowing through the stent 18 or the pressure of the hardenable material in the outer filling structure 12. In other embodiments, the pressure filled in the inner filling structure 16 may be less than the outer filling structure 12.

As shown in FIG. 9, the shape of the inner filling structure 16 in various embodiments is that of an elongated tube that has a substantially equal outer diameter from one end to another. The inner filling structure 16 has a lumen for blood flow at approximately the center of the inner filling structure 16. Accordingly, the distance between the inner wall of the inner filling structure 16 and an outer perimeter of the stent remains similar through substantially the entire length of the inner filling structure 16, unless impinged by the anatomy, thrombus or aortic wall. The outer filling structure 12 is intended to expand like a balloon, if needed, to occupy the volume within the aneurysm to prevent endoleaks (Type I or II).

Figure 10:
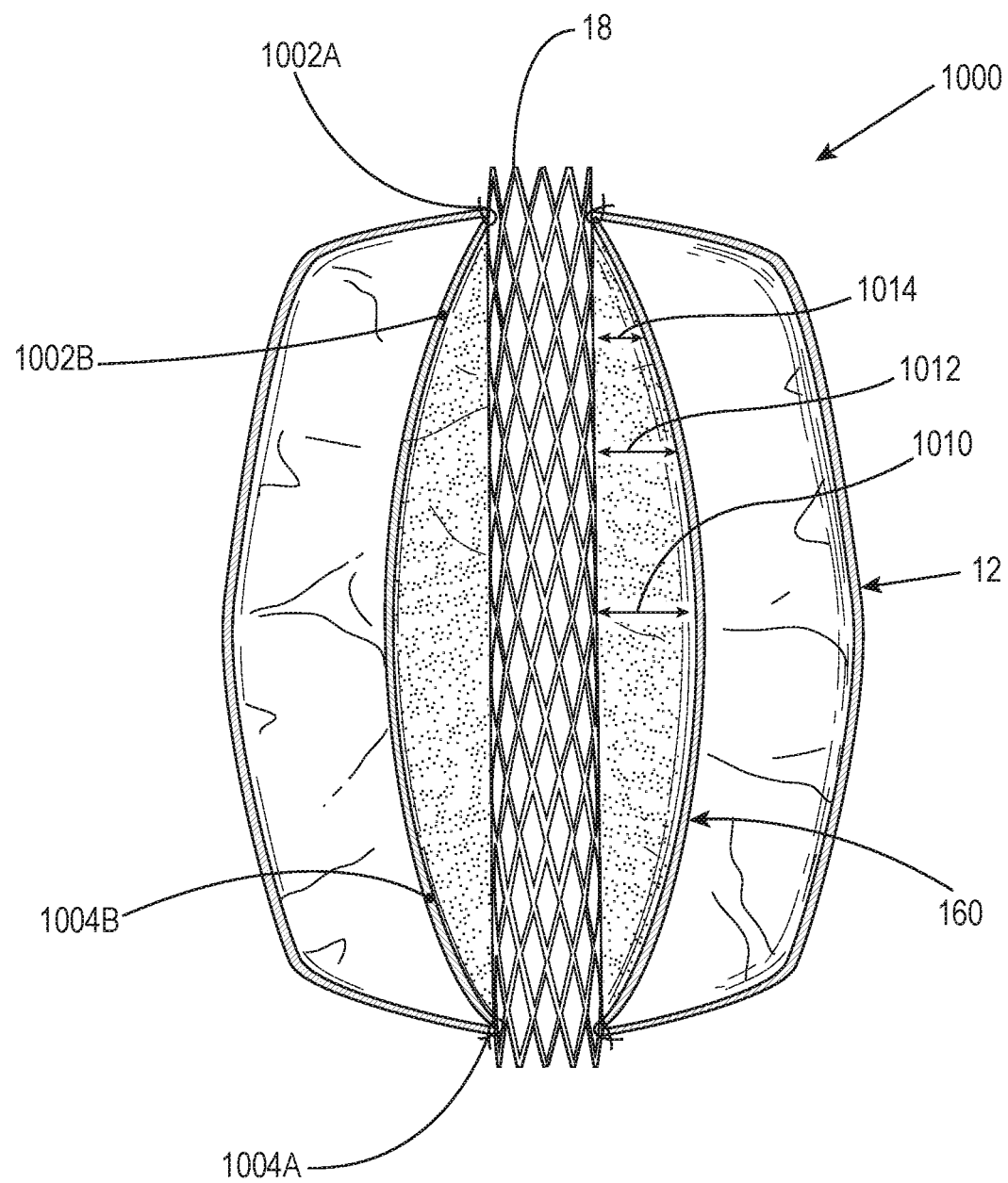
FIG. 10 is an illustration of a dual inflatable single prosthesis in accordance with an illustrative embodiment.

FIG. 10 illustrates another embodiment of a dual inflatable prosthesis 1000. Dual inflatable prosthesis 1000 comprises an outer filling structure 12, an inner filling structure 160, a stent 18, sutures 1002A, and sutures 1004A. Dual inflatable prosthesis 1000 has features that are similar to the dual inflatable prosthesis shown in FIGS. 1B and FIG. 9. In the embodiment shown in FIG. 10, the inner filling structure 160 may be shaped differently than the shape of the inner filling structure 16 of FIGS. 1B and 9. For example, as shown in FIG. 10, the inner filling structure 160 may be oval shaped around the blood lumen such that the distance between the outer wall and the inner wall of the inner filling structure 160 increases or decreases along the length of the inner filling structure 160. The oval shape of the inner filling structure 160 assures that the hardenable filling material provides greatest support to the stent 18 at the middle section, center, or mid region of the stent 18. Providing support to the stent 18 with the inner filling structure 160 may add columnar strength to the stent 18 and prevent migration or bending of the stent 18 against pulsatile forces. The oval shape of the inner filling structure 160 may reduce the radial cross section of the dual inflatable prosthesis 1000 at the ends of the device where an example fill line may be located.

In various embodiments, the inner filling structure 160 may have a distance 1010 between the outer wall of the inner filling structure 160 and the inner wall of the inner filling structure 160. As shown in FIG. 9, a distance between the outer wall of the inner filling structure and the inner wall of the inner filling structure 160 may be reduced from the distance 1010 to distance 1012 to distance 1014 along a length of the inner filling structure 160. In various embodiments, the inner filling structure 160 and the outer filling structure 12 may be attached to the stent 18 using heat bonding, glue bonding, welding, sutures or other suitable attachment mechanisms at the proximal and distal end of the dual inflatable prosthesis 1000. At the distal end of the stent 18, the sutures 1004A may be used to secure the outer filling structure 12 and the inner filling structure 160 to the stent 18. In other embodiments, only sutures 1002A may be used to secure the proximal end of the stent 18.

In other embodiments, the outer filling structure 12 may be attached to the inner filling structure 160 at location 1002B and location 1004B that are located away from the proximal and distal ends of the stent 18. In various embodiments, the outer filling structure 12 may be configured to expand like a balloon to occupy the volume within the aneurysm. In some embodiments, the outer filling structure 12 may apply minimal pressure against the aneurysm wall. The higher pressurization of the inner filling structure 160 is configured to allow the dual inflatable prosthesis 1000 to achieve wall opposition and seal against proximal and distal ends of the aneurysm.

Figure 11:
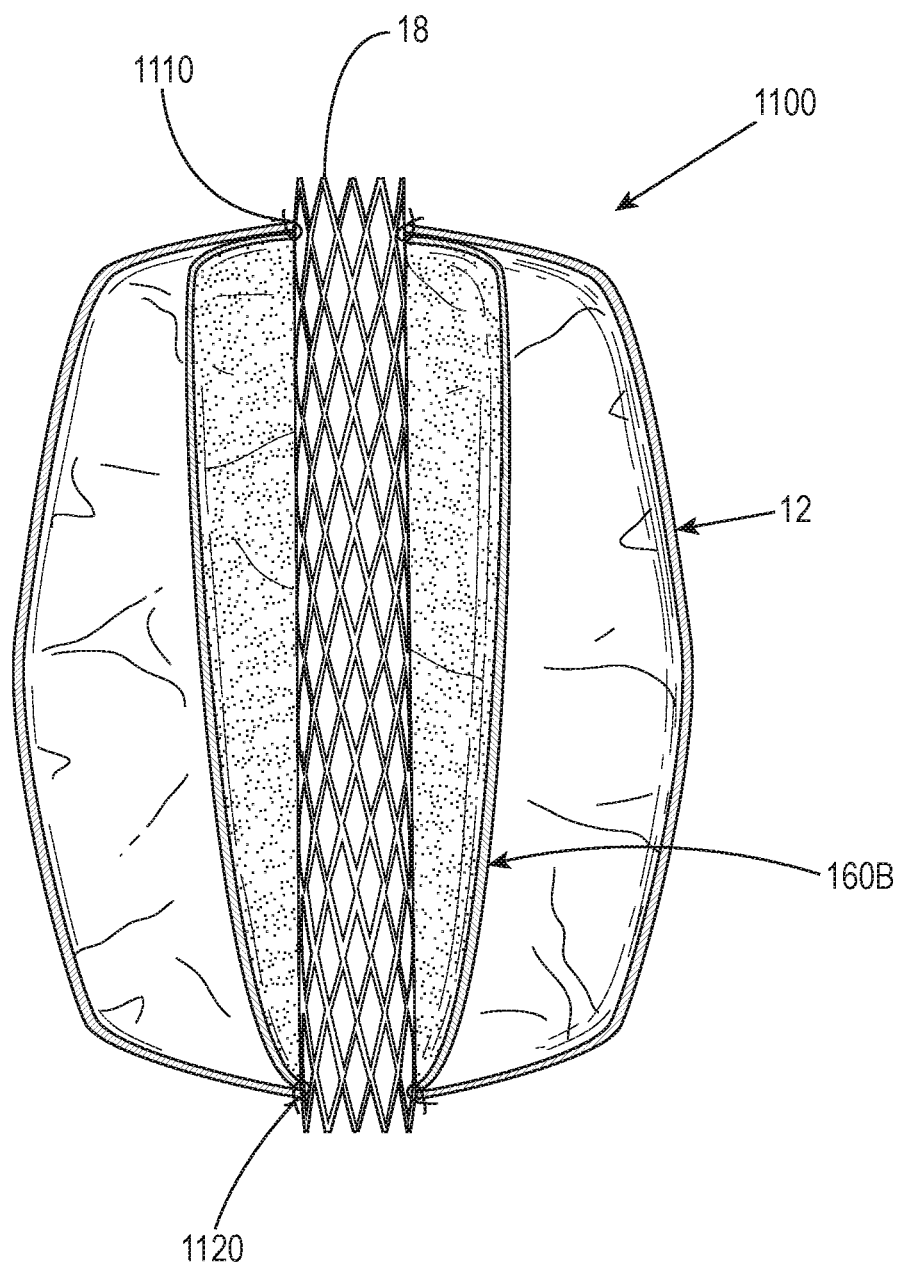
FIG. 11 is an illustration of a dual inflatable single prosthesis in accordance with an illustrative embodiment.

FIG. 11 illustrates a dual inflatable prosthesis 1100. The dual inflatable prosthesis 1100 is similar to the prostheses illustrated in FIGS. 1B, 9, and 10. The dual inflatable prosthesis 1100 includes an outer filling structure 12, a stent 18 and an inner filling structure 160B. The inner filling structure 160B may be attached to the stent 18 at the proximal end using sutures 1110. The distal end of the inner filling structure 160B may be attached to the distal end of the stent 18 using sutures 1120. In the embodiment shown in FIG. 11, a diameter of the inner filling structure 160B around the stent 18 decreases from the proximal end to the distal end. In this embodiment, the dual inflatable prosthesis 1100 achieves greater wall opposition on the proximal end of the aneurysm which reduces a radial profile for insertion into a catheter. The change in the shape of the inner filling structure 160B from being a larger radius to a smaller radius assists the dual inflatable prosthesis 1100 achieve appropriate proximal placement while bringing the aneurysm from healthy aortic tissue to healthy aortic tissue. In various embodiments, the inner filling structure 160B is made of a material that takes a predetermined shape that does not change after a certain amount of pressure is achieved until failure pressure above 800 mm Hg or higher is reached.

Figure 12A:
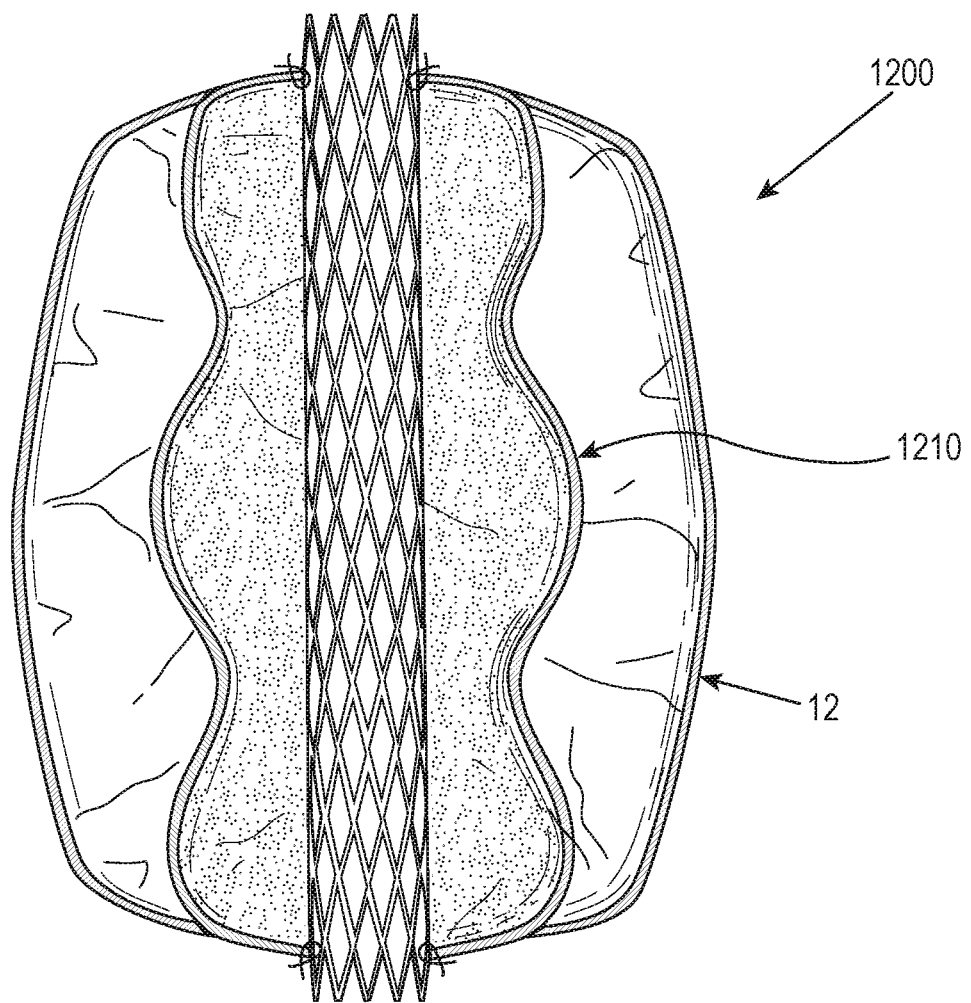
FIG. 12A is an illustration of a dual inflatable single prosthesis in accordance with an illustrative embodiment.

FIG. 12A illustrates a dual inflatable prosthesis 1200 that includes an inner filling structure 1210 and an outer filling structure 12. FIG. 12A shows the inner filling structure 1210 that changes a diameter of an outer wall of the inner filling structure 1210 across a length dimension of the inner filling structure 1210. As shown in FIG. 12A, the outer filling structure 12 is attached to the outer wall of the inner filling structure 1210.

Figure 12B:
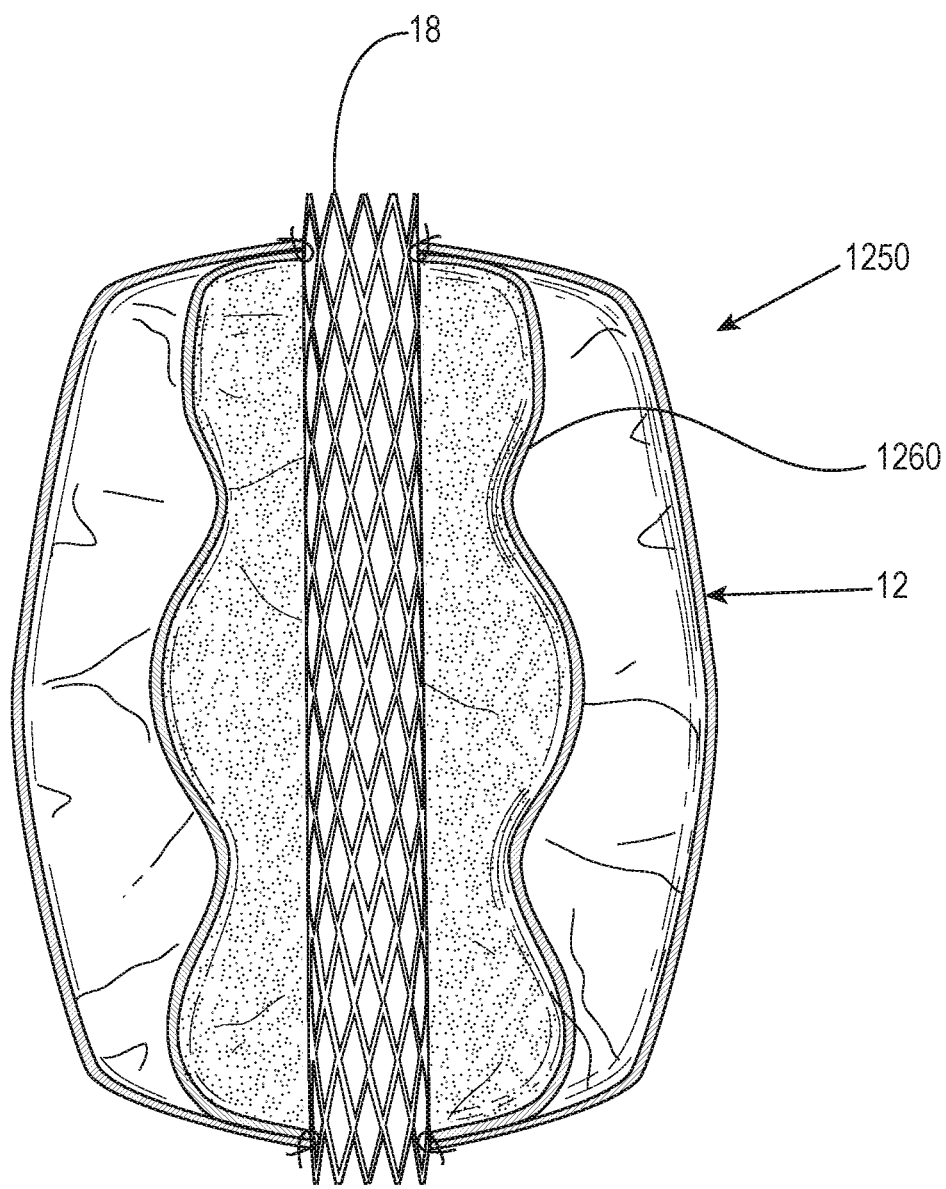
FIG. 12B is an illustration of a dual inflatable single prosthesis in accordance with an illustrative embodiment.

FIG. 12B illustrates a dual inflatable prosthesis 1250 that includes an inner filling structure 1260 and an outer filling structure 12. FIG. 12B shows the inner filling structure 1260 that changes a diameter of the outer wall of the inner filling structure 1260 along a length dimension of the inner filling structure 1260. As shown in FIG. 12B the outer filling structure 12 may be attached to a stent 18 directly with the use of sutures on the proximal and distal ends of the dual inflatable prosthesis 1250.

Figure 13A:
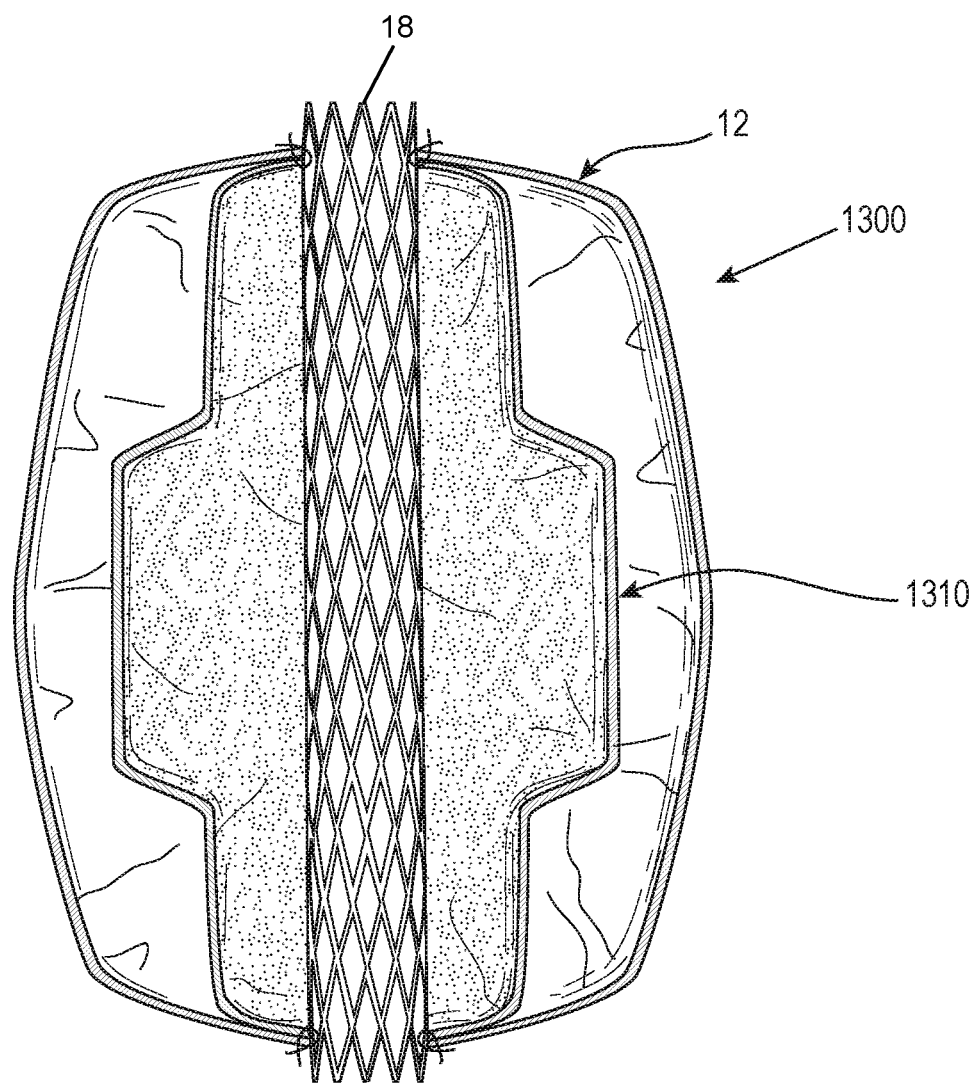
FIG. 13A is an illustration of a dual inflatable single prosthesis in accordance with an illustrative embodiment.

FIG. 13A illustrates a dual inflatable prosthesis 1300 that includes an inner filling structure 1310 and an outer filling structure 12. FIG. 13A shows the inner filling structure 1310 that changes a diameter of the outer wall of the inner filling structure 1310 to be wider at a center of a stent 18 along a length dimension of the inner filling structure 1310. As shown in FIG. 13A the outer filling structure 12 may be attached to the stent 18 directly with the use of sutures on the proximal and distal ends of the dual inflatable prosthesis 1300.

Figure 13B:
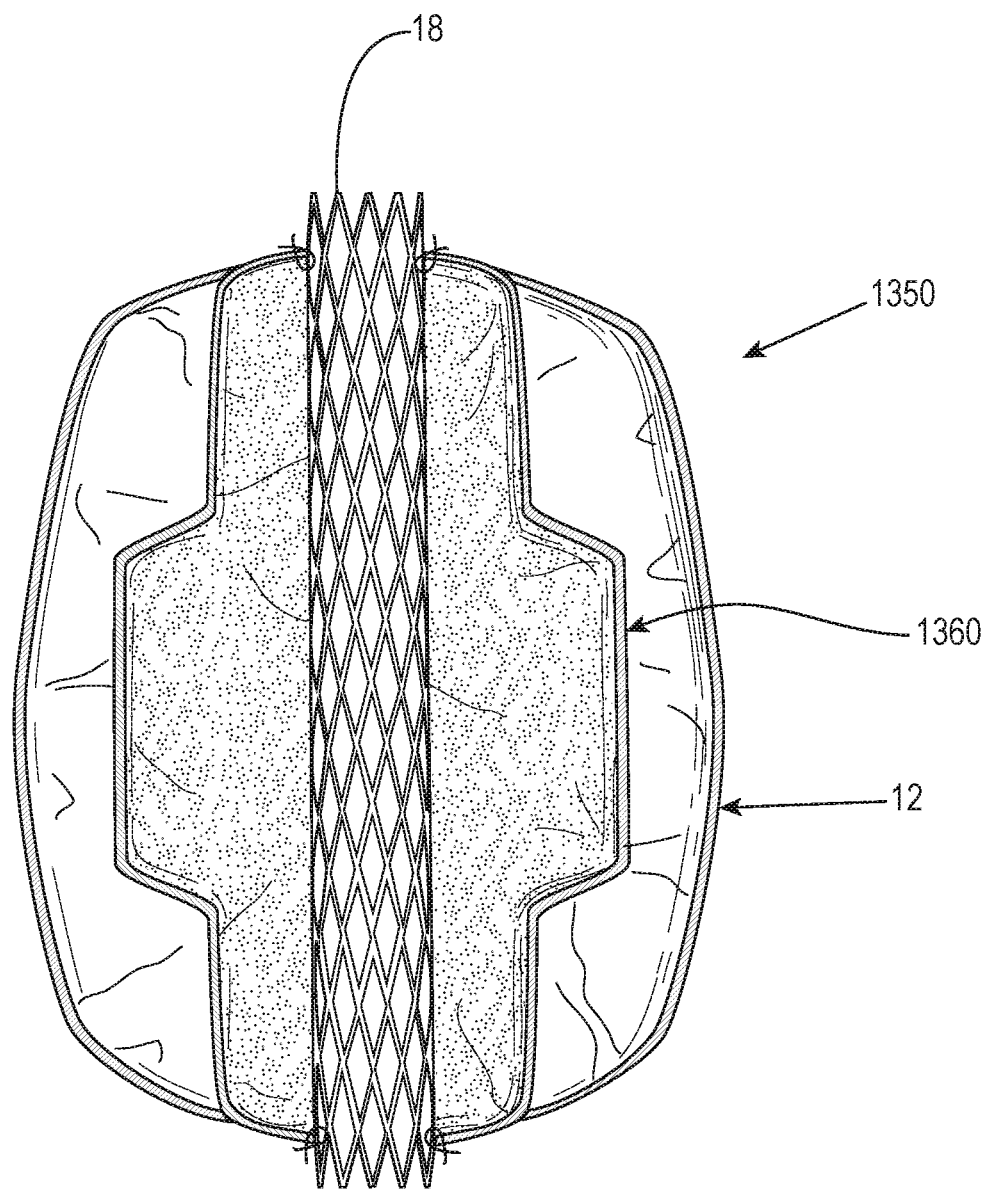
FIG. 13B is an illustration of a dual inflatable single prosthesis in accordance with an illustrative embodiment.

FIG. 13B illustrates a dual inflatable prosthesis 1350 that includes an inner filling structure 1360 and an outer filling structure 12. FIG. 13B shows the inner filling structure 1360 that changes a diameter of the outer wall of the inner filling structure 1360 along a length dimension of the inner filling structure 1360. As shown in FIG. 13B, the outer filling structure 12 may be attached to the outer wall of the inner filling structure 1360.

Figure 14A:
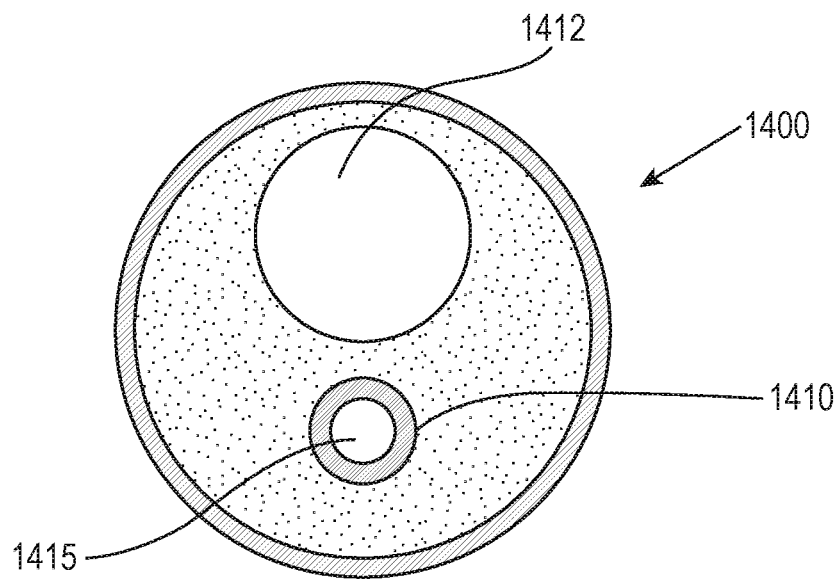
FIG. 14A is an illustration of a fill line in accordance with an illustrative embodiment.

FIG. 14A illustrates a cross sectional view of a catheter 1400 that includes a guide wire lumen 1412, an outer fill line 1410, and an inner fill line 1415. In various embodiments, a fill line may be a flexible tube that is connected on one end to a liquid polymer dispensing apparatus that is located outside the patient with the aneurysm. The other end of the fill line may be connected to any of the inner filling structures or the outer filling structures described herein. The embodiment shown FIG. 14A illustrates concentric fill lines. For example, the outer fill line 1410 surrounds the inner fill line 1415. The inner fill line 1415 may extend beyond the outer fill line 1410 in a length direction.

Figure 14B:
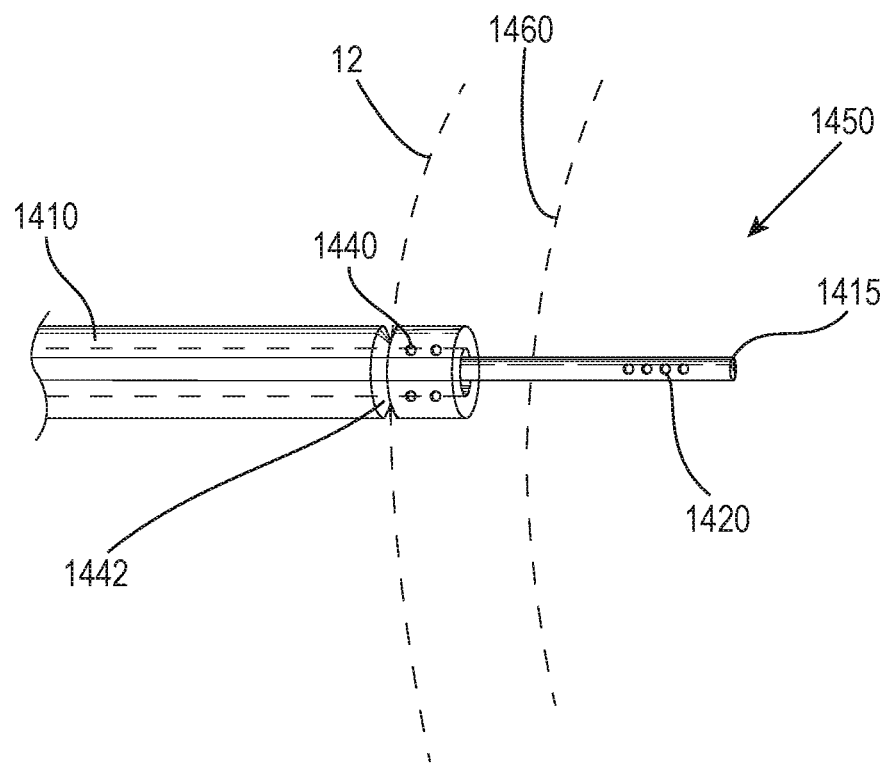
FIG. 14B is an illustration of a fill line in accordance with the illustrative embodiment shown in FIG. 14A.

FIG. 14B illustrates a fill line 1450. The inner fill line 1415 has holes 1420 that are located in an inner filling structure 1460. The outer fill line 1410 has holes 1440 that are located within the outer filling structure 12. FIG. 14B also illustrates a tear away 1442 that allows a user to separate the fill line 1450.

Figure 15A:
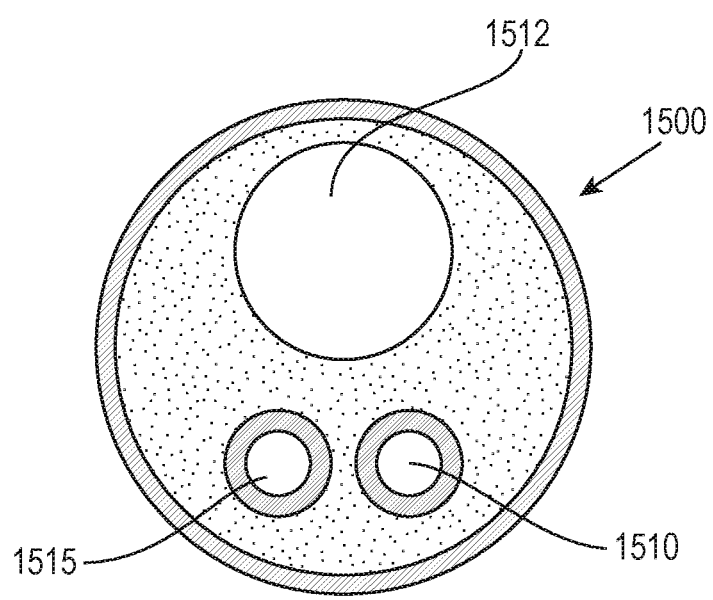
FIG. 15A is an illustration of a fill line in accordance with an illustrative embodiment.

FIG. 15A illustrates a catheter 1500 that includes a guide wire lumen 1512, an inner fill line 1510, and an outer fill line 1515. FIG. 15A shows two fill lines on a side by side basis. In various embodiments, the inner fill line 1510 is longer than the outer fill line 1515. The inner fill line 1515 is connected to an inner filling structure as described above in various figures. The outer fill line 1515 may be connected to an outer filling structure as described above in various figures.

Figure 15B:
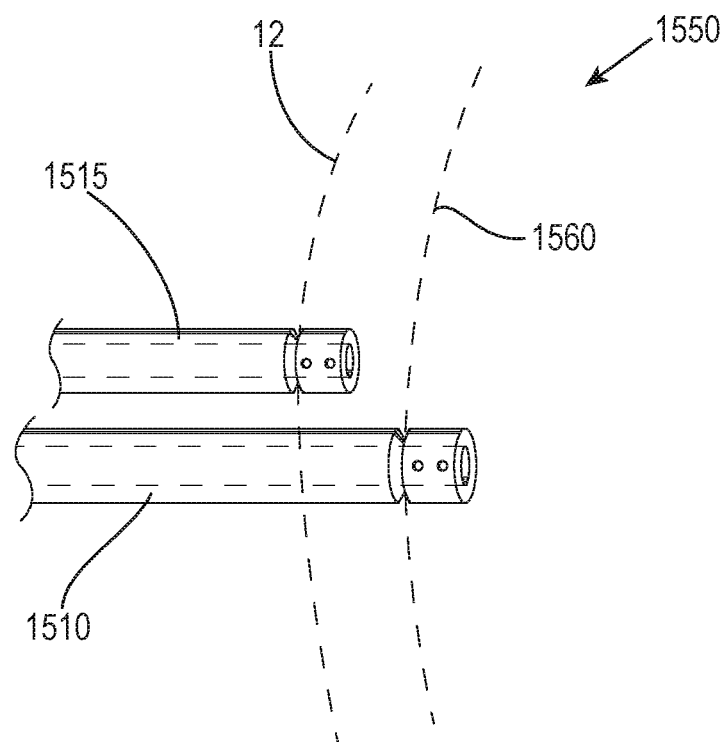
FIG. 15B is an illustration of a fill line in accordance with the illustrative embodiment shown in FIG. 15A.

FIG. 15B illustrates a fill line 1550 that includes side by side fill lines. For example, the inner fill line 1510 may be connected to an inner filling structure 1560. The outer fill line 1515 may be connected to the outer filling structure 12. In various embodiments, both fill lines 1510 and 1515 are configured to provide a liquid hydrogel into the appropriate filling structures. Both fill lines 1510 and 1515 may have a tear away that allows the fill lines to be detached from the corresponding filling structures.

In some embodiments, the inner filling structure of the embodiments described above comprises an inner bag that may also be implemented with circumferentially restrictive elements on its outer diameter (and potentially on the inner diameter as well) that would allow the inner bag to be filled to higher pressure while retaining a shape consistent with the luminal course of the native anatomy. In various embodiments, this feature would prevent "straightening" of tortuous anatomy as a result of a concentric high pressure non-compliant balloon's characteristic of longitudinal rigidity when inflated to higher pressures. The inner bag might also embody a component within its inner wall that provides sufficient resistance to dilatation.

In various embodiments, the outer filling structure of the embodiments described above comprises an outer bag that may originate and terminate as close to the proximal and distal edge of the inner bag as possible. In some embodiments, the outer bag may be offset from the inner bag. The outer bag may be made of a highly compliant material similar in properties to a latex balloon. As such, the inner diameter of the outer bag may be defined by the outer diameter of the inner bag. In various embodiments, the outer bag may be sufficiently compliant to not require redundancy or folding in its manufactured state or in the delivery system itself.

The inner and outer bag sealing sequence may occur in the following manner. The inner bag may be initially filled with a filling medium and allowed to cure. Information is acquired from imaging, pressure readings or other observable measurements to confirm optimal position and sealing of the inner bag component. The outer bag may be filled to a pressure consistent with its intended purpose to obliterate the aneurysmal sac of liquid blood and seal at pressures appropriate to that function and in light of the more vulnerable status of the more diseased and dilated tissue present in the mid-aneurysmal sac.

The filling mechanism would include designs to allow a single filling lumen that could differentially fill the inner bag followed by the outer bag through either a partial withdrawal of the filling tube from the higher pressure environment of the inner bag to the lumen of the outer bag or a coaxial system that allowed withdrawal of an inner lumen that terminated in the lumen of the inner bag such that the outer coaxial lumen was exposed to the lumen of the outer bag. Another embodiment of the filling mechanism would be separate filling lumens to both the inner and outer bags each of which could be coaxial such that a primary and secondary fill and/or pressure assessment could be made. Separate filling lumens would also allow for redundancy of the sealing system in the event of technical problems with either one of the bags or either of the filling lumens.

In various embodiments, various graft materials may line the interior surface of the inner bag. If the inner bag inner wall is not constructed in a manner sufficient to prevent chronic dilatation or expansion of the luminal diameter, then the graft material lining the inner lumen of the inner bag would serve as both a biocompatible blood interface and a structural element to prevent chronic dilatation of the blood flow lumen beyond the original extent of the blood lumen created at the time of implant. If the inner wall of the inner bag incorporates a mechanical element sufficient to resist chronic dilatation, then any graft material used to line the blood flow lumen would have no structural role but rather an interface or surface interaction role.

The function, purpose and features of a dual compliance/pressure sealing system may include wall tension that is a function of the pressure present within the containment and the shape of the containment. Wall tension may be higher in areas with larger diameter and is focally higher as a function of multiple geometric variables encountered in the morphologic changes the aorta expresses as a manifestation of aneurysmal dilatation.

A single compliance/pressure system may create uniform pressure when distended by the sealing component and thus creates the highest wall tension in the most dilated and contorted segments of the aorta or iliac arteries affected by the aneurysmal process. The presence of an aortic defect (i.e. clinical presentation of aneurysm rupture) can prevent the ability of a single compliance/pressure sealing system from developing the pressure necessary to create an effective and therefore therapeutic seal. The most proximal and distal segments of the treatment zone are less dilated and likely to withstand the higher pressures that would ensure most effective sealing. The inner bag of dual compliance/pressure sealing system is designed to create a highly effective seal using higher pressures that are compatible with less diseased and dilated arterial segments. In various embodiments, the non-compliant nature of the inner bag prevents it from extending beyond a defined diameter and therefore prevents higher pressures from being exerted on arterial segments beyond a defined diameter in either the aorta or iliac arterial segments or extending into rupture defects of the arterial segment.

The ability to inflate the inner bag to a defined and higher pressure will create proximal and distal seal zones without any pressure being exerted on weakest areas of the aneurysmal segment. The above system, in various embodiments, enables better use of the sealing technology to keep intact the ruptured aneurysmal segments as its containment and pressurization is only dependent on non-dilated and relatively healthier arterial segments and the non-compliant nature of the balloon across arterial segments larger than it's diameter.

The primary inflation of the inner bag will stabilize the entire system at an earlier stage of the procedure facilitating the treatment of both intact and ruptured aneurysms and also facilitating the positioning of the proximal and distal ends of the sealing system. The maintenance of that position is provided through the completion of the procedure to include the filling of the outer bag that occurs after the inner bag has cured to its final state.

In various embodiments, the compliance of the outer bag may act as a smooth outer surface of the sealing system as it is not intended to be folded or redundant in any manner. The outer bag could be constructed such that in its initial state it is already somewhat "stretched" so that it assists in containing and maintaining the delivery diameter of the inner bag and other inner elements of the sealing system.

Various advantages may be realized with the various embodiments described herein. In various embodiments, the inner bag comprises an Endobag. Also, in various embodiments, the outer bag comprises an Endobag. The devices described herein (stent and Endobag) may be deployed with precision using the device described herein or by using radio opaque markers embedded within each of the filling structures at the proximal end of the bag and the distal end of the bag. The filling structures or Endobag may be prevented from prolapsing by providing a non-compliant high pressure bag adjacent to the stent. The Endobag may create robust seal in normal vascular segments with use of relatively Higher-Pressures (up to 500 mm Hg) with a differential pressure filling device. In various embodiments, robust polymer encapsulation of the stent provides stent-stability and positional integrity. Various embodiments of the systems and devices described herein will allow a physician the ability to treat a patient with a ruptured aneurysm by bridging the gap between the healthy tissue with the inner filling structure.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments.

What is claimed is:

1. A system, comprising:
   an inner filling structure configured to be inflated with a hardenable material to produce a first seal with a first portion of an artery at a first end of the inner filling structure; and
   an outer filling structure having an inner surface that surrounds at least a portion of the inner filling structure, the outer filling structure inflatable to occupy a space within an aneurysm wherein the inner filling structure is configured such that a diameter of the inner filling structure varies along a length of the inner filling structure when the inner filling structure is in an inflated state.

2. The system of claim 1,
wherein the inner filling structure is inflatable to produce a second seal with a second portion of the artery at a second end of the inner filling structure.

3. The system of claim 1,
wherein a pressure within the inner filling structure when the inner filling structure is in an inflated state is higher than a pressure within the outer filling structure when the outer filling structure is in an inflated state.

4. The system of claim 1,
wherein the inner filling structure comprises a semi-compliant material that is less compliant than a material of the outer filling structure.

5. The system of claim 1,
wherein the inner filling structure is configured to be inflatable to a pressure in a range of 300 to 600 mm Hg; and
wherein the outer filling structure is configured to be inflatable to a pressure in a range of 50 to 120 mm Hg.

6. The system of claim 1,
wherein the inner filling structure is fillable with a hardenable material to a pressure that is higher than a pressure in the outer filling structure.

7. The system of claim 1,
wherein the inner filling structure is configured to overlap a healthy region of the artery that is proximal the aneurysm.

8. The system of claim 1,
wherein the outer filling structure is configured to contact a wall of the aneurysm after being filled to a pressure that is lower than a pressure in the inner filling structure.

9. The system of claim 1,
wherein the inner filling structure has a hardness of at least about 55D shore-A.

10. The system of claim 1,
wherein the outer filling structure has a hardness of at least about 70 shore-A or 77 shore-A.

11. A system, comprising:
a stent;
an inner filling structure attached to the stent, the inner filling structure inflatable with a filling medium;
an outer filling structure having an inner surface that surrounds at least a portion of the inner filling structure, the outer filling structure inflatable to occupy a space within an aneurysm;
a first fill line connected to the inner filling structure; and
a second fill line connected to the outer filling structure.

12. A system, comprising:
a stent;
an inner filling structure attached to the stent, the inner filling structure inflatable with a filling medium; and
an outer filling structure having an inner surface that surrounds at least a portion of the inner filling structure, the outer filling structure inflatable to occupy a space within an aneurysm;
wherein the inner filling structure is configured such that a diameter of a proximal end of the inner filling structure is greater than a diameter of a distal end of the inner filling structure when the inner filling structure is in an inflated state.

13. A system, comprising:
a stent;
an inner filling structure attached to the stent, the inner filling structure inflatable with a filling medium; and
an outer filling structure having an inner surface that surrounds at least a portion of the inner filling structure, the outer filling structure inflatable to occupy a space within an aneurysm,
wherein the inner filling structure is configured such that a diameter of the inner filling structure varies along a length of the inner filling structure when the inner filling structure is in an inflated state.

* * * * *